US012639815B2

(12) United States Patent
Qiao et al.

(10) Patent No.: US 12,639,815 B2
(45) Date of Patent: May 26, 2026

(54) SPECTRAL IMAGE-BASED SKINCARE DEVICE AND METHOD FOR RESIDUE DETECTION AND TREATMENT

(71) Applicant: Dyson Technology Limited, Wiltshire (GB)

(72) Inventors: Tong Qiao, Bristol (GB); Andrew Collingwood Watson, Gloucester (GB)

(73) Assignee: Dyson Technology Limited, Malmesbury (GB)

( * ) Notice: Subject to any disclaimer, the term of this patent is extended or adjusted under 35 U.S.C. 154(b) by 276 days.

(21) Appl. No.: 18/566,232

(22) PCT Filed: May 26, 2022

(86) PCT No.: PCT/GB2022/051333
§ 371 (c)(1),
(2) Date: Dec. 1, 2023

(87) PCT Pub. No.: WO2022/254187
PCT Pub. Date: Dec. 8, 2022

(65) Prior Publication Data
US 2024/0249410 A1 Jul. 25, 2024

(30) Foreign Application Priority Data
Jun. 4, 2021 (GB) .................................... 2108028

(51) Int. Cl.
*G06T 7/00* (2017.01)
*A61B 5/00* (2006.01)

(52) U.S. Cl.
CPC .......... *G06T 7/0012* (2013.01); *A61B 5/0075* (2013.01); *G06T 2207/30088* (2013.01)

(58) Field of Classification Search
CPC ......... G06T 7/0012; G06T 2207/30088; A61B 5/0075; A61B 5/441; A61B 2018/0047;
(Continued)

(56) References Cited

U.S. PATENT DOCUMENTS

2005/0154382 A1 7/2005 Altshuler et al.
2006/0129209 A1 6/2006 McDaniel
(Continued)

FOREIGN PATENT DOCUMENTS

CN 105572007 A 5/2016
CN 108323911 A 7/2018
(Continued)

OTHER PUBLICATIONS

International Search Report and Written Opinion received for PCT Patent Application No. PCT/GB2022/051333, mailed on Sep. 6, 2022, 14 pages.
(Continued)

*Primary Examiner* — Christopher Wait
(74) *Attorney, Agent, or Firm* — Tucker Ellis LLP

(57) ABSTRACT

A skincare device including a spectral sensor configured to capture a spectral image of a subject at one or more wavelengths outside of the visible spectrum; and a controller is provided. The controller is configured to analyse the spectral image to determine a measure of cosmetic residue present on the subject; and control the skincare device to perform an action associated with the determined measure of cosmetic residue. Also provided is a method and computer programme for the device.

18 Claims, 19 Drawing Sheets

(58) Field of Classification Search
CPC .... A61B 2018/00642; A45D 2044/007; A61N
2005/0628; A61N 5/0616; A61N 5/06;
G01J 3/42
See application file for complete search history.

(56) References Cited

U.S. PATENT DOCUMENTS

| | | | |
|---|---|---|---|
| 2010/0185064 A1* | 7/2010 | Bandic | A61B 5/444 |
| | | | 600/306 |
| 2015/0230863 A1 | 8/2015 | Youngquist et al. | |
| 2015/0287191 A1* | 10/2015 | Koruga | A61B 5/444 |
| | | | 382/128 |

FOREIGN PATENT DOCUMENTS

| | | | |
|---|---|---|---|
| EP | 2389573 A2 | 11/2011 | |
| WO | 2010/093503 A2 | 8/2010 | |

OTHER PUBLICATIONS

Search Report received for GB Application No. 2108028.8, mailed on Nov. 24, 2021, 1 page.

* cited by examiner

<u>Fig. 3</u>

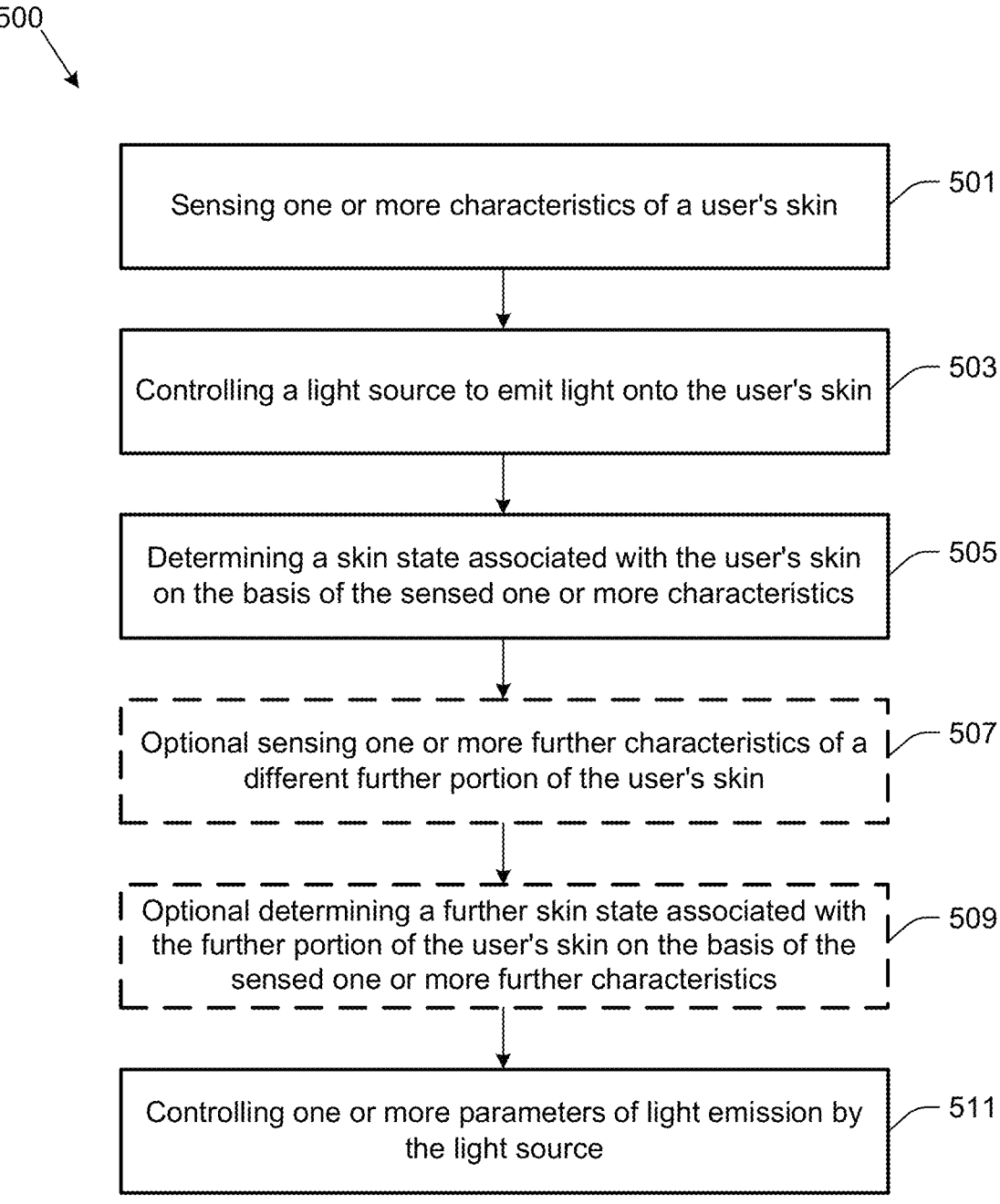

500

Sensing one or more characteristics of a user's skin — 501

Controlling a light source to emit light onto the user's skin — 503

Determining a skin state associated with the user's skin on the basis of the sensed one or more characteristics — 505

Optional sensing one or more further characteristics of a different further portion of the user's skin — 507

Optional determining a further skin state associated with the further portion of the user's skin on the basis of the sensed one or more further characteristics — 509

Controlling one or more parameters of light emission by the light source — 511

Fig. 5

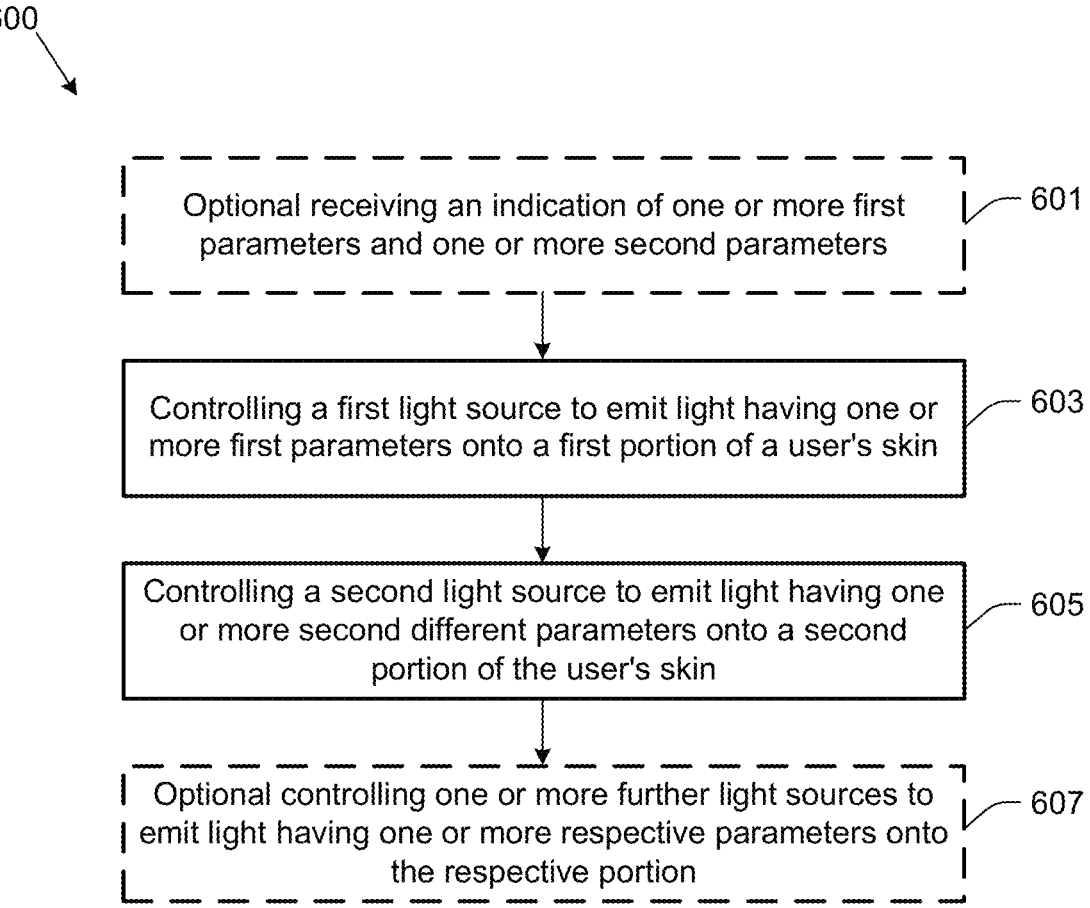

600

Optional receiving an indication of one or more first parameters and one or more second parameters — 601

Controlling a first light source to emit light having one or more first parameters onto a first portion of a user's skin — 603

Controlling a second light source to emit light having one or more second different parameters onto a second portion of the user's skin — 605

Optional controlling one or more further light sources to emit light having one or more respective parameters onto the respective portion — 607

Fig. 6

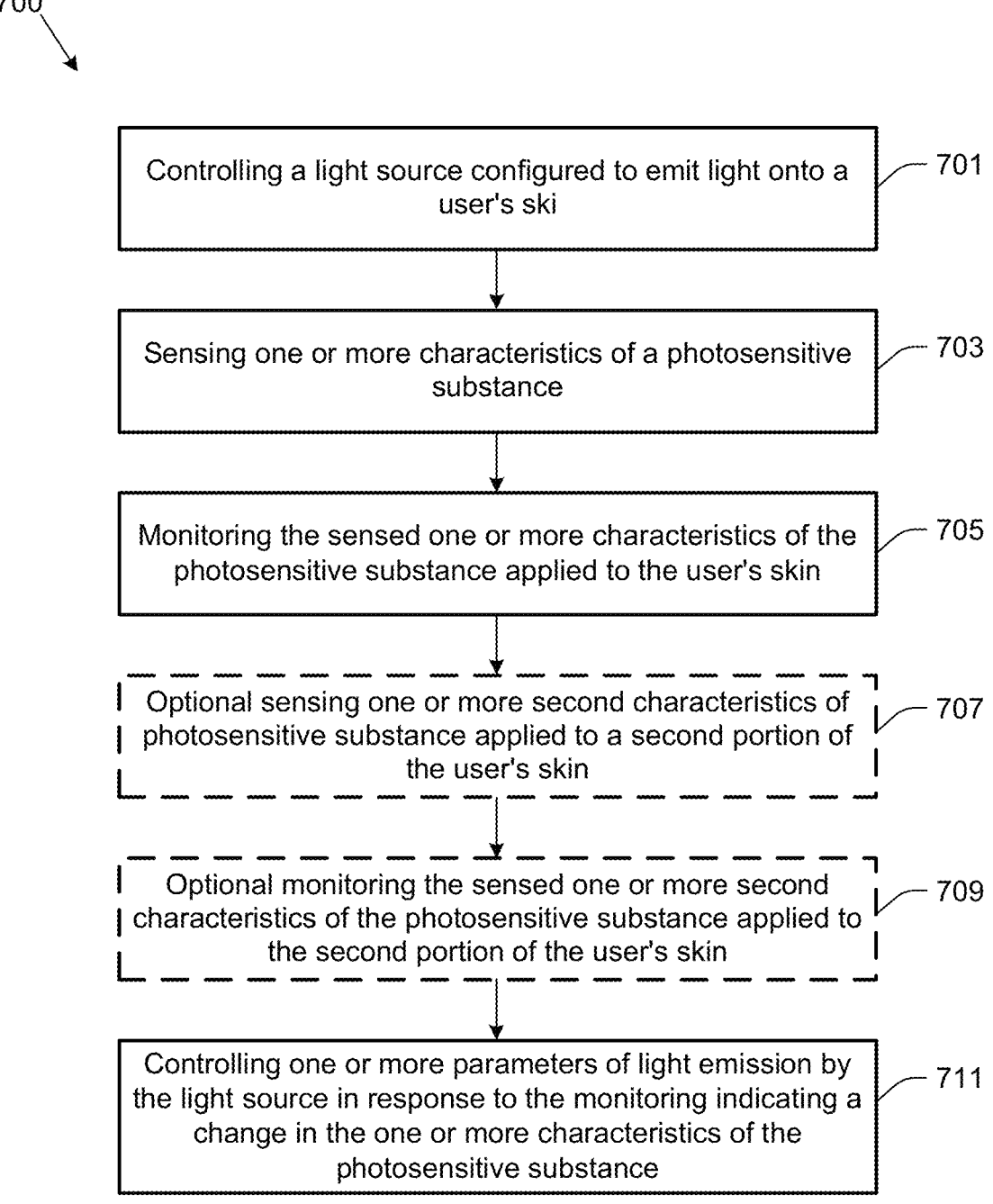

700

Controlling a light source configured to emit light onto a user's ski — 701

Sensing one or more characteristics of a photosensitive substance — 703

Monitoring the sensed one or more characteristics of the photosensitive substance applied to the user's skin — 705

Optional sensing one or more second characteristics of photosensitive substance applied to a second portion of the user's skin — 707

Optional monitoring the sensed one or more second characteristics of the photosensitive substance applied to the second portion of the user's skin — 709

Controlling one or more parameters of light emission by the light source in response to the monitoring indicating a change in the one or more characteristics of the photosensitive substance — 711

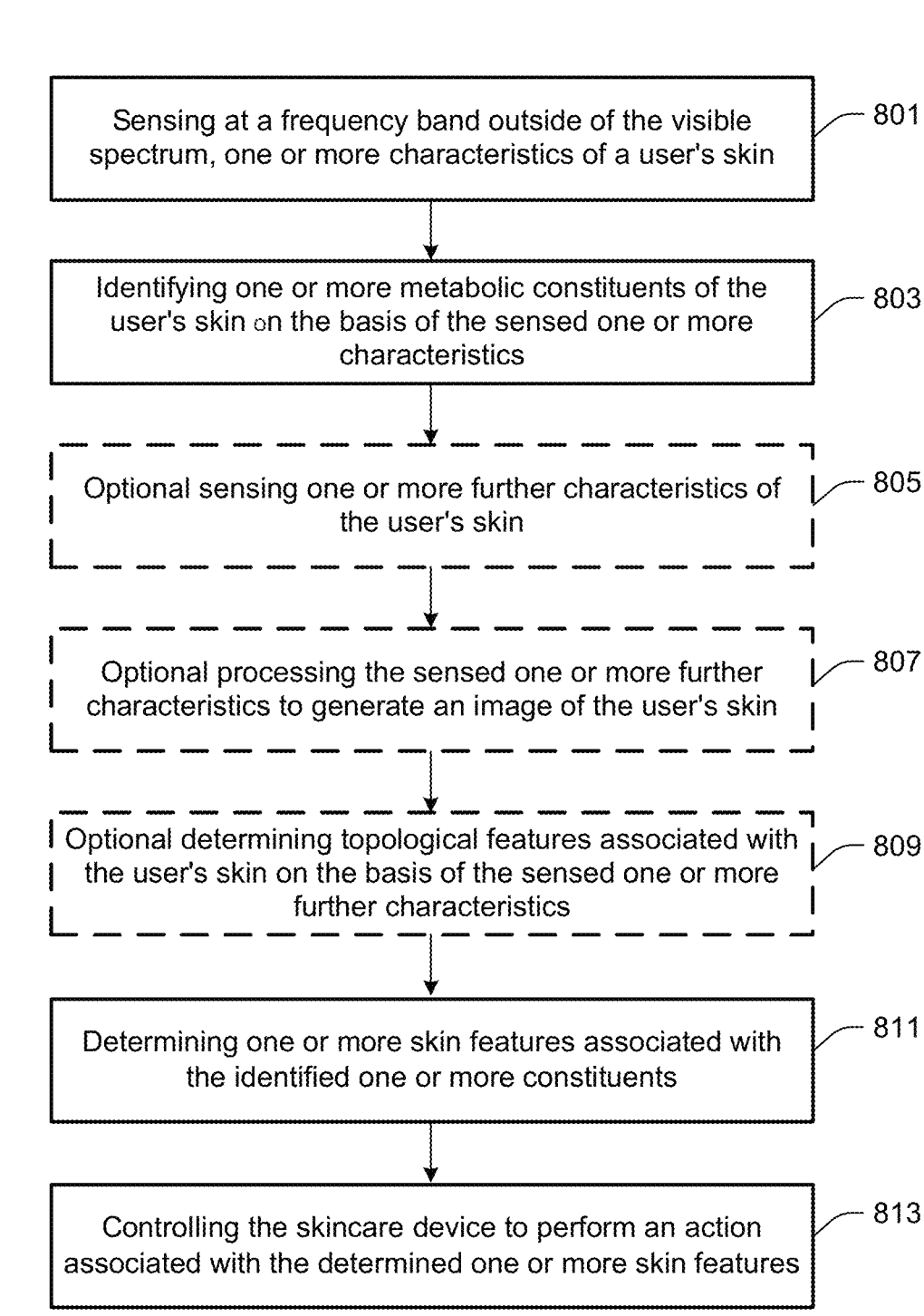

Sensing at a frequency band outside of the visible spectrum, one or more characteristics of a user's skin ⟋ 801

Identifying one or more metabolic constituents of the user's skin on the basis of the sensed one or more characteristics ⟋ 803

Optional sensing one or more further characteristics of the user's skin ⟋ 805

Optional processing the sensed one or more further characteristics to generate an image of the user's skin ⟋ 807

Optional determining topological features associated with the user's skin on the basis of the sensed one or more further characteristics ⟋ 809

Determining one or more skin features associated with the identified one or more constituents ⟋ 811

Controlling the skincare device to perform an action associated with the determined one or more skin features ⟋ 813

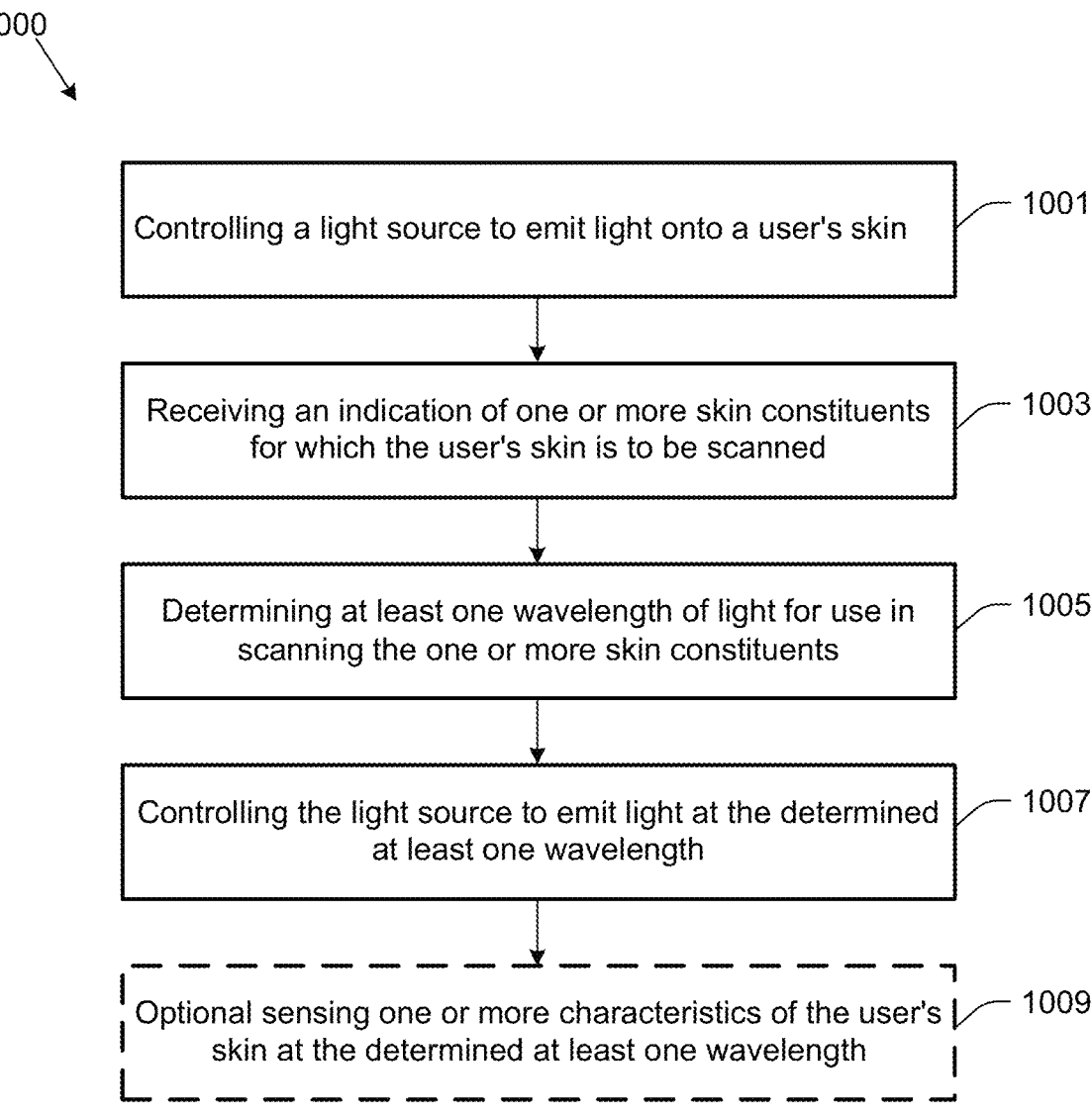

Controlling a light source to emit light onto a user's skin — 1001

Receiving an indication of one or more skin constituents for which the user's skin is to be scanned — 1003

Determining at least one wavelength of light for use in scanning the one or more skin constituents — 1005

Controlling the light source to emit light at the determined at least one wavelength — 1007

Optional sensing one or more characteristics of the user's skin at the determined at least one wavelength — 1009

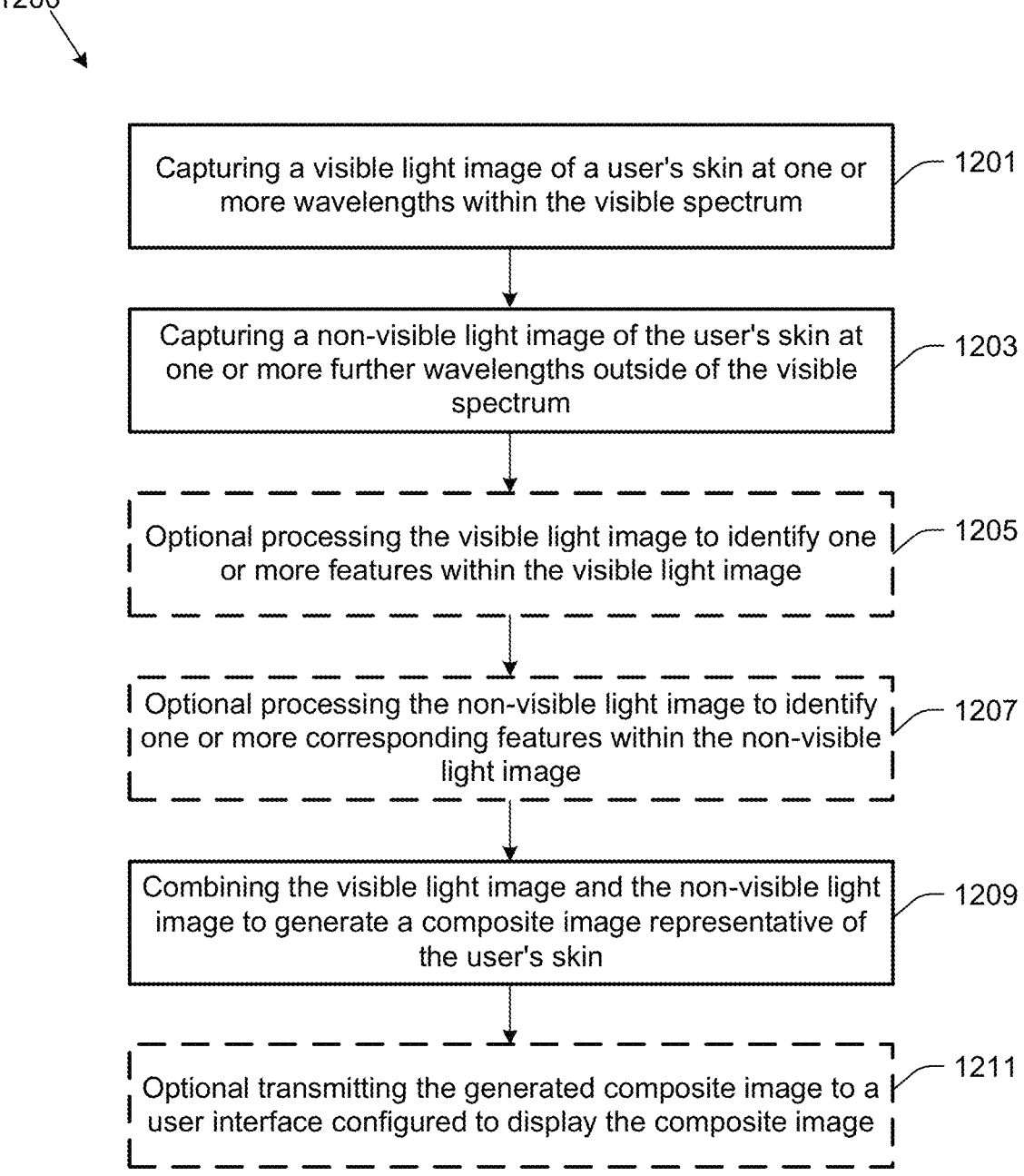

Capturing a visible light image of a user's skin at one or more wavelengths within the visible spectrum — 1201

Capturing a non-visible light image of the user's skin at one or more further wavelengths outside of the visible spectrum — 1203

Optional processing the visible light image to identify one or more features within the visible light image — 1205

Optional processing the non-visible light image to identify one or more corresponding features within the non-visible light image — 1207

Combining the visible light image and the non-visible light image to generate a composite image representative of the user's skin — 1209

Optional transmitting the generated composite image to a user interface configured to display the composite image — 1211

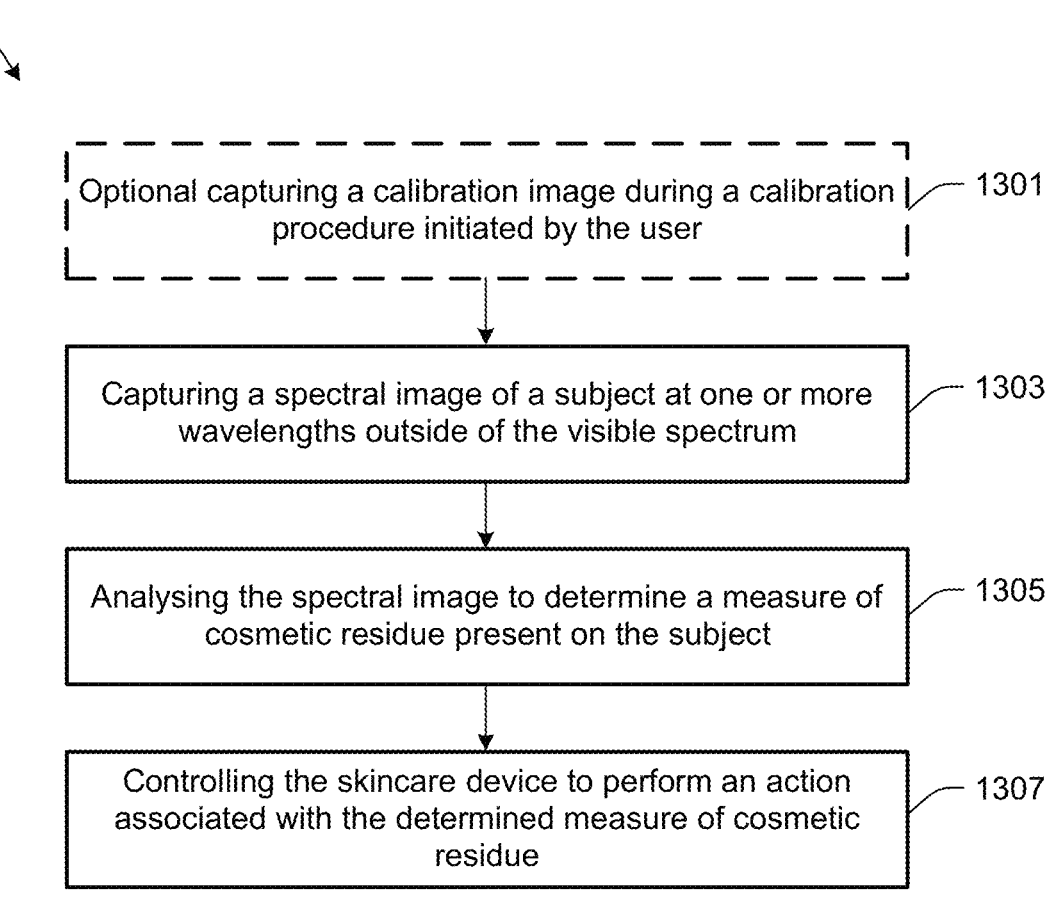

Optional capturing a calibration image during a calibration procedure initiated by the user — 1301

Capturing a spectral image of a subject at one or more wavelengths outside of the visible spectrum — 1303

Analysing the spectral image to determine a measure of cosmetic residue present on the subject — 1305

Controlling the skincare device to perform an action associated with the determined measure of cosmetic residue — 1307

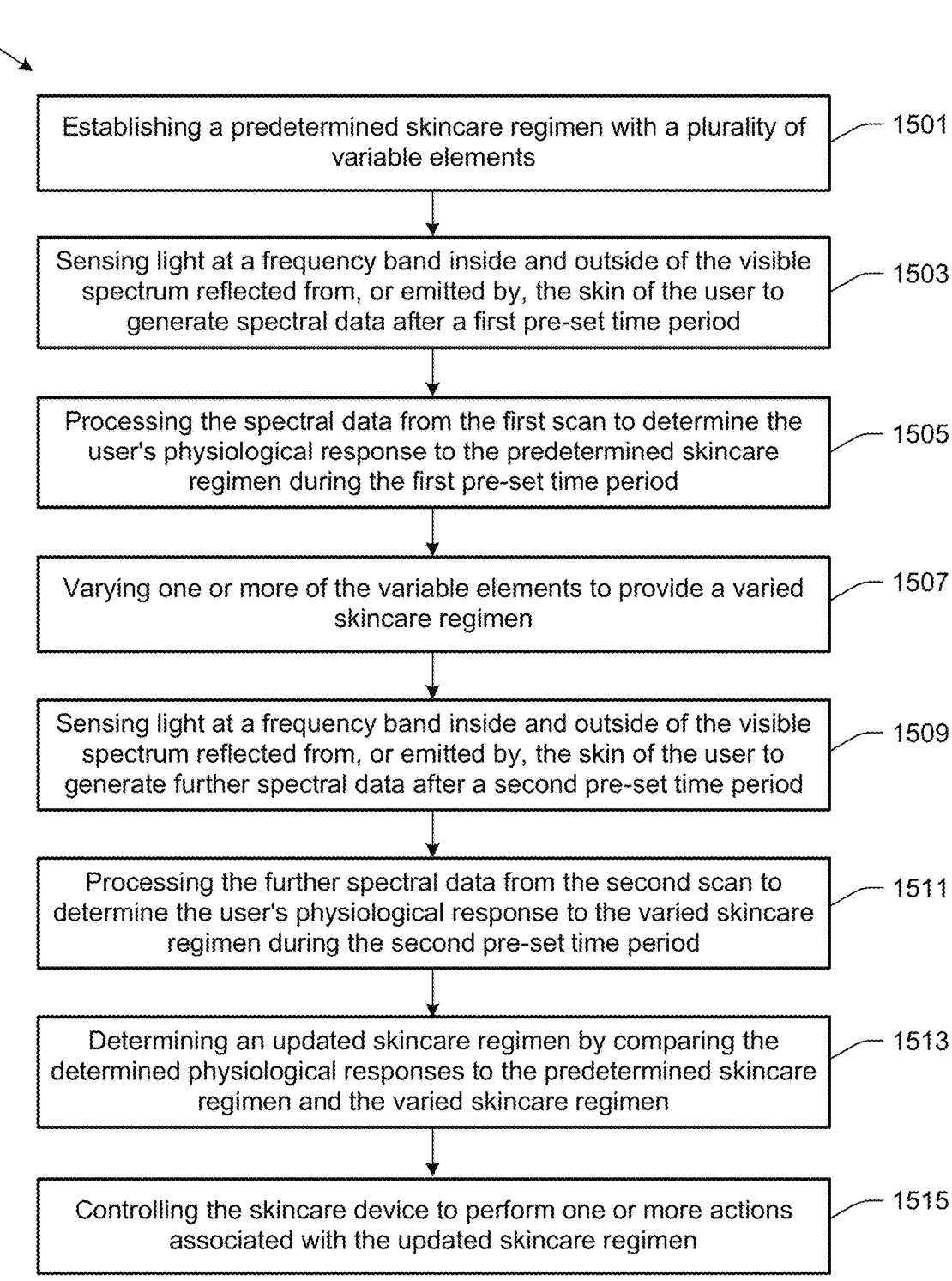

Establishing a predetermined skincare regimen with a plurality of variable elements — 1501

Sensing light at a frequency band inside and outside of the visible spectrum reflected from, or emitted by, the skin of the user to generate spectral data after a first pre-set time period — 1503

Processing the spectral data from the first scan to determine the user's physiological response to the predetermined skincare regimen during the first pre-set time period — 1505

Varying one or more of the variable elements to provide a varied skincare regimen — 1507

Sensing light at a frequency band inside and outside of the visible spectrum reflected from, or emitted by, the skin of the user to generate further spectral data after a second pre-set time period — 1509

Processing the further spectral data from the second scan to determine the user's physiological response to the varied skincare regimen during the second pre-set time period — 1511

Determining an updated skincare regimen by comparing the determined physiological responses to the predetermined skincare regimen and the varied skincare regimen — 1513

Controlling the skincare device to perform one or more actions associated with the updated skincare regimen — 1515

Fig. 15

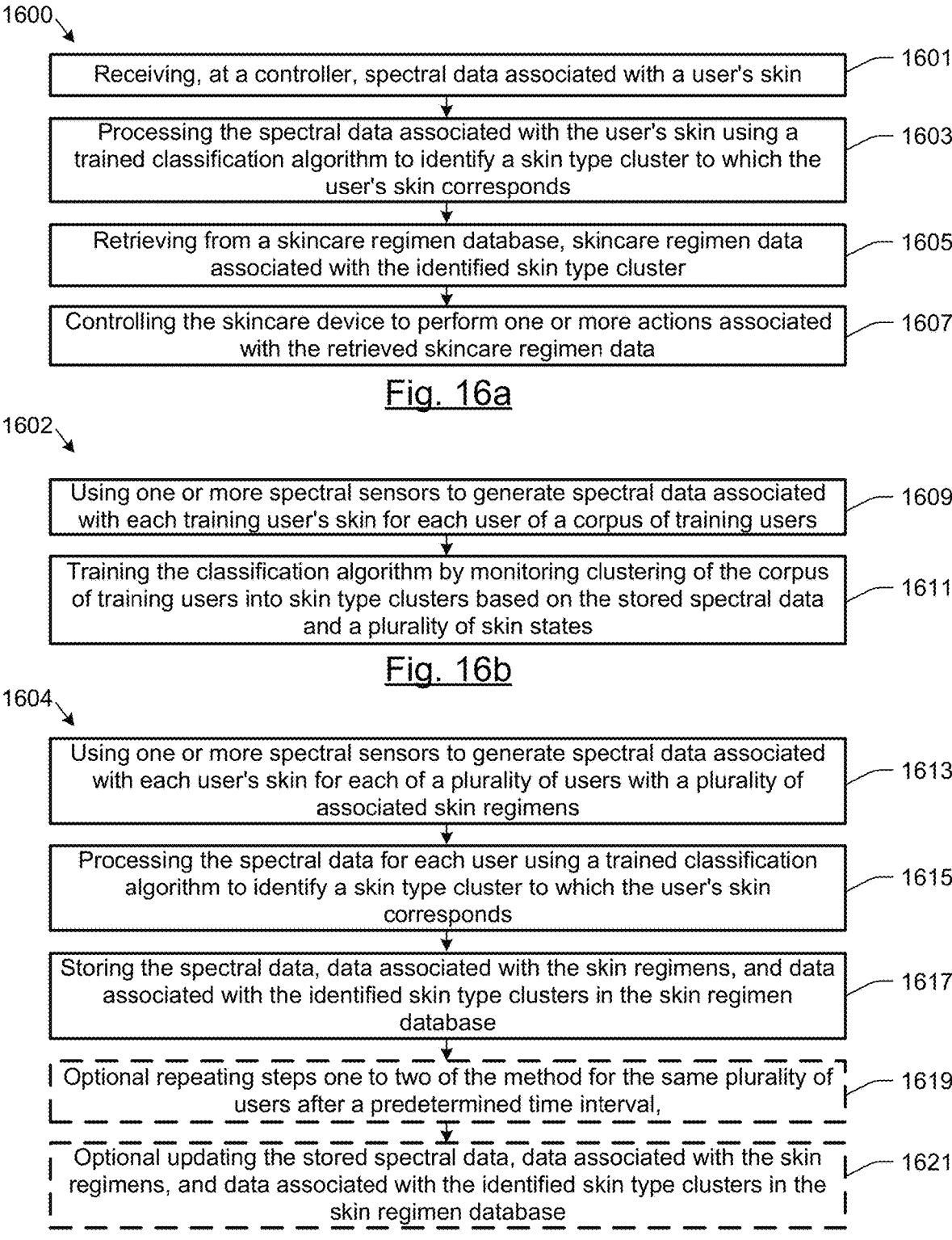

1600

| Receiving, at a controller, spectral data associated with a user's skin | 1601 |

| Processing the spectral data associated with the user's skin using a trained classification algorithm to identify a skin type cluster to which the user's skin corresponds | 1603 |

| Retrieving from a skincare regimen database, skincare regimen data associated with the identified skin type cluster | 1605 |

| Controlling the skincare device to perform one or more actions associated with the retrieved skincare regimen data | 1607 |

| Using one or more spectral sensors to generate spectral data associated with each training user's skin for each user of a corpus of training users | 1609 |

| Training the classification algorithm by monitoring clustering of the corpus of training users into skin type clusters based on the stored spectral data and a plurality of skin states | 1611 |

| Using one or more spectral sensors to generate spectral data associated with each user's skin for each of a plurality of users with a plurality of associated skin regimens | 1613 |

| Processing the spectral data for each user using a trained classification algorithm to identify a skin type cluster to which the user's skin corresponds | 1615 |

| Storing the spectral data, data associated with the skin regimens, and data associated with the identified skin type clusters in the skin regimen database | 1617 |

| Optional repeating steps one to two of the method for the same plurality of users after a predetermined time interval, | 1619 |

| Optional updating the stored spectral data, data associated with the skin regimens, and data associated with the identified skin type clusters in the skin regimen database | 1621 |

Fig. 16c

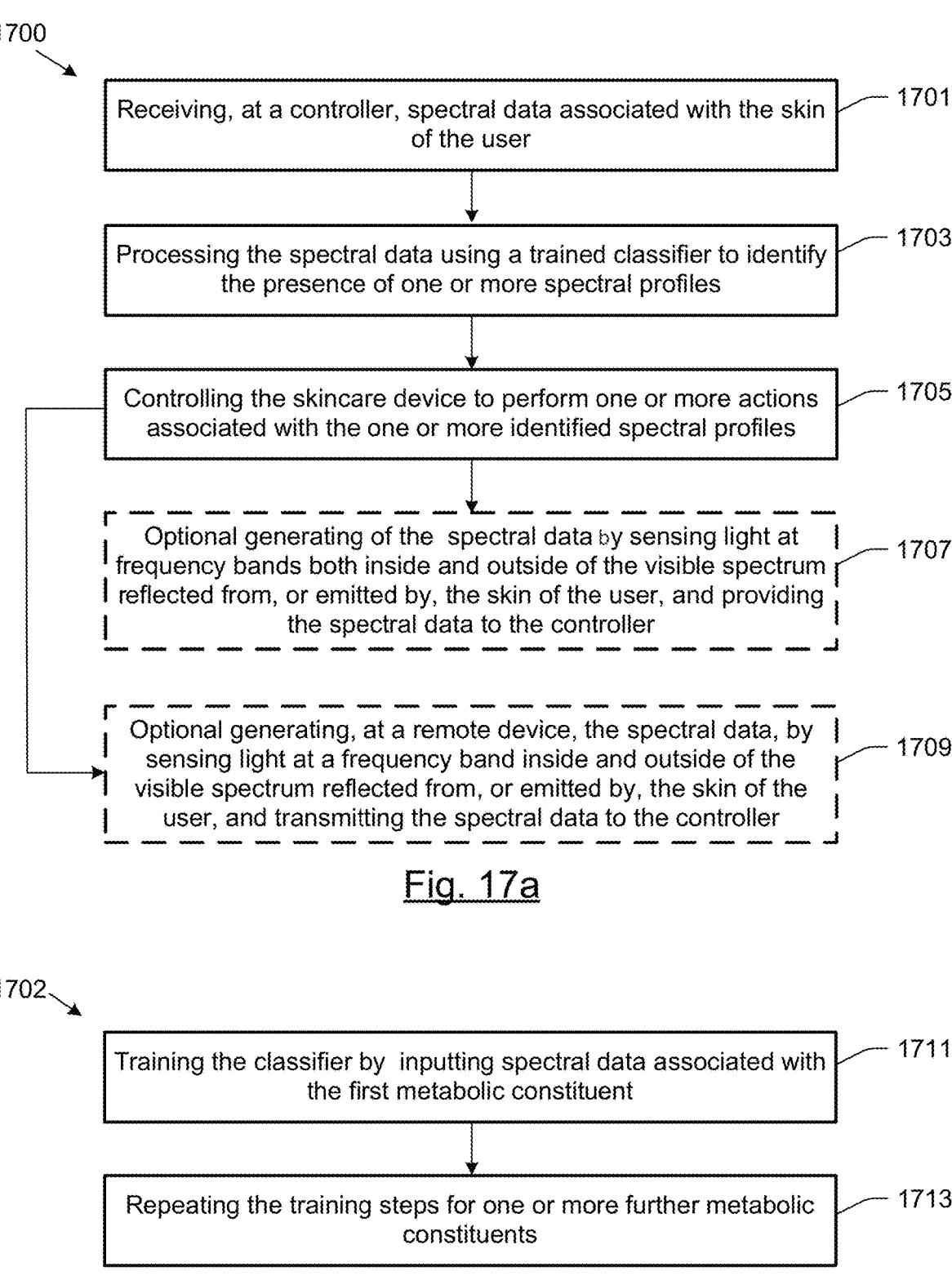

1700

Receiving, at a controller, spectral data associated with the skin of the user — 1701

Processing the spectral data using a trained classifier to identify the presence of one or more spectral profiles — 1703

Controlling the skincare device to perform one or more actions associated with the one or more identified spectral profiles — 1705

Optional generating of the spectral data by sensing light at frequency bands both inside and outside of the visible spectrum reflected from, or emitted by, the skin of the user, and providing the spectral data to the controller — 1707

Optional generating, at a remote device, the spectral data, by sensing light at a frequency band inside and outside of the visible spectrum reflected from, or emitted by, the skin of the user, and transmitting the spectral data to the controller — 1709

Training the classifier by inputting spectral data associated with the first metabolic constituent — 1711

Repeating the training steps for one or more further metabolic constituents — 1713

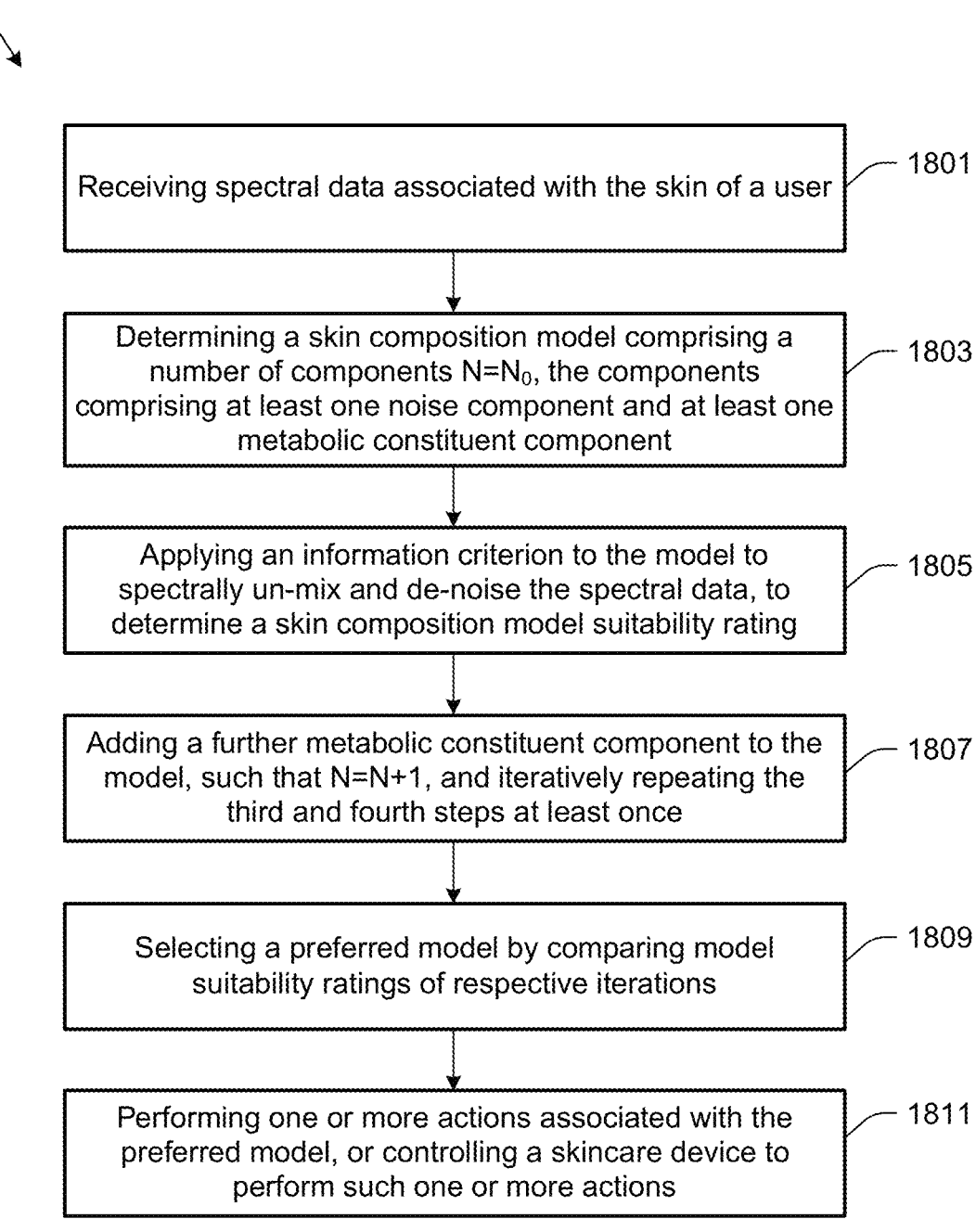

Receiving spectral data associated with the skin of a user — 1801

Determining a skin composition model comprising a number of components $N=N_0$, the components comprising at least one noise component and at least one metabolic constituent component — 1803

Applying an information criterion to the model to spectrally un-mix and de-noise the spectral data, to determine a skin composition model suitability rating — 1805

Adding a further metabolic constituent component to the model, such that $N=N+1$, and iteratively repeating the third and fourth steps at least once — 1807

Selecting a preferred model by comparing model suitability ratings of respective iterations — 1809

Performing one or more actions associated with the preferred model, or controlling a skincare device to perform such one or more actions — 1811

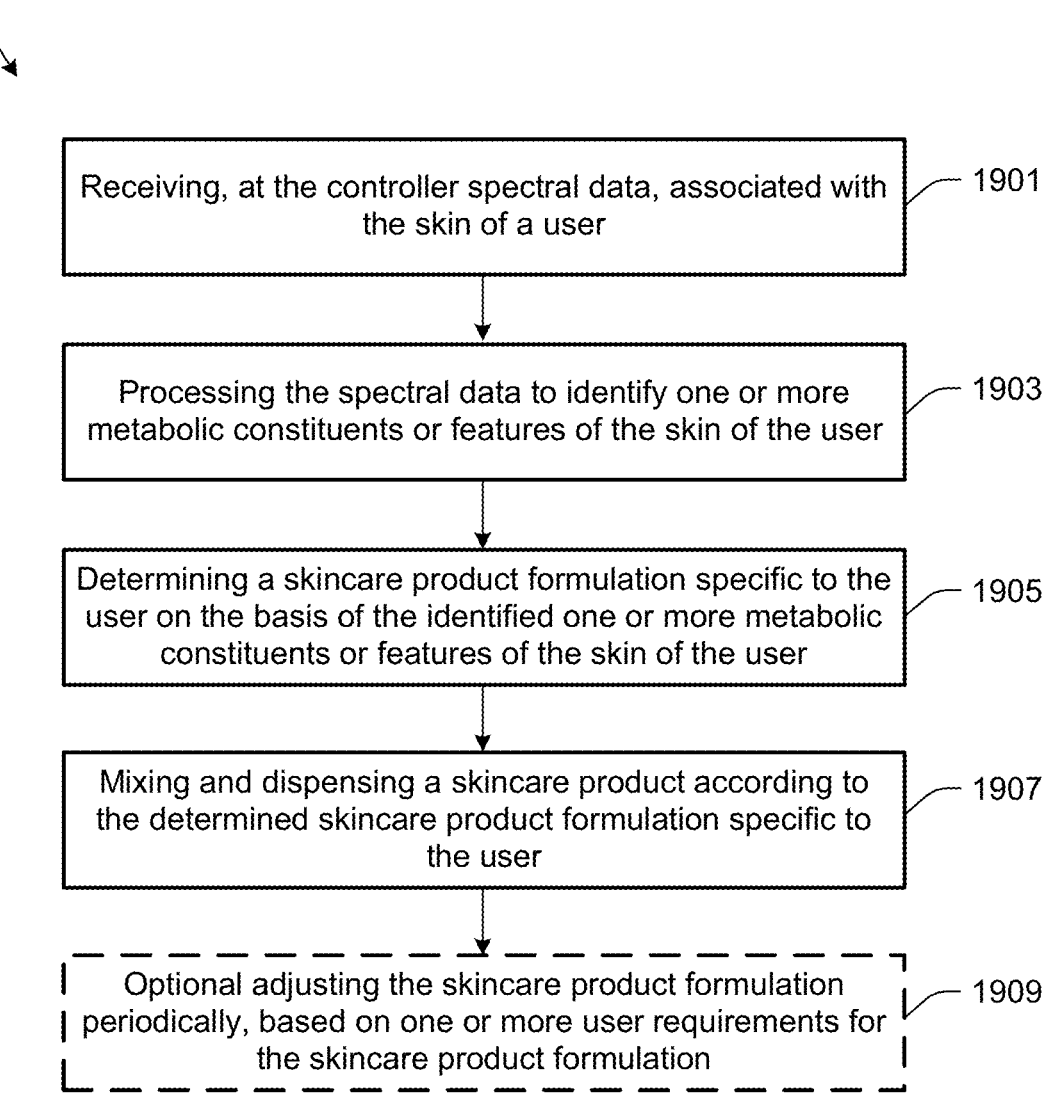

Receiving, at the controller spectral data, associated with the skin of a user ⟋ 1901

Processing the spectral data to identify one or more metabolic constituents or features of the skin of the user ⟋ 1903

Determining a skincare product formulation specific to the user on the basis of the identified one or more metabolic constituents or features of the skin of the user ⟋ 1905

Mixing and dispensing a skincare product according to the determined skincare product formulation specific to the user ⟋ 1907

Optional adjusting the skincare product formulation periodically, based on one or more user requirements for the skincare product formulation ⟋ 1909

Fig. 19

SPECTRAL IMAGE-BASED SKINCARE DEVICE AND METHOD FOR RESIDUE DETECTION AND TREATMENT

CROSS-REFERENCE TO PRIOR APPLICATIONS

This application is the National Stage of International Application No. PCT/GB2022/051333 filed May 26, 2022, and claims benefit of United Kingdom Application No. 2108028.8 filed Jun. 4, 2021, each of which are herein incorporated by reference in their entirety.

TECHNICAL FIELD

The present disclosure concerns skincare devices and methods of operating a skincare device. The present disclosure also concerns the use of a photosensitive substance.

BACKGROUND

Cosmetic compositions have long been used to attempt to improve the condition and state of a user's skin. More recently, cosmetic phototherapeutic treatments have been proposed as a means to improve the state of a user's skin. Phototherapeutic treatments involve exposing the user's skin to wavelengths of light which have been demonstrated to yield a therapeutic effect on the user's skin.

Ideally, a user's specific cosmetic treatment regime (for example, utilising one or both of cosmetic compositions and phototherapeutic treatment) would be identified by a dermatologist during an assessment of the user's skin. More typically, however, the user is not able to or it is inconvenient for a user to consult a dermatologist, and must instead make an assessment of their own skin and skincare needs without expert assistance. However, such users are typically not experts in skincare, and must therefore devote significant time and effort to identifying their cosmetic skincare issues and determining causes of and possible remedies for those issues. Furthermore, because of a lack of expertise and the complexity in assessing and remedying cosmetic skin issues, there is no guarantee that even the most diligent of users is capable of accurately making such an assessment. Therefore, users run the risk of incorrectly identifying their cosmetic skin issues and taking inappropriate or unnecessary remedial actions.

The present disclosure seeks to mitigate the above-mentioned problems. Alternatively or additionally, the present disclosure seeks to provide an improved skincare device and methods of operating a skincare device.

SUMMARY

According to a first aspect of the present disclosure there is provided a skincare device comprising:

a spectral sensor configured to capture a spectral image of a subject at one or more wavelengths outside of the visible spectrum; and a controller configured to:

analyse the spectral image to determine a measure of cosmetic residue present on the subject; and control the skincare device to perform an action associated with the determined measure of cosmetic residue.

By capturing a spectral image of a subject at one or more wavelengths outside of the visible spectrum and analysing the spectral image, it is possible to determine a measure of cosmetic residue (for example, makeup) present on the subject. This enables the device to assist a user in removing cosmetic products from the subject (for example, by identifying a location on the subject of residual cosmetic product). Furthermore, by comparing the quantities of cosmetic residue remaining on the subject following different cleansing/makeup removal compositions or routines, the device provides means to compare the effectiveness of those cleansing/makeup removal compositions or routines.

In embodiments, determining a measure of cosmetic residue comprises identifying a portion of the spectral image having the lowest received signal strength at the one or more wavelengths. In embodiments, the controller is configured to determine, for each of one or more further portions of the spectral image, a relative quantity of cosmetic residue by calculating a relative signal strength compared to the identified lowest signal strength.

By identifying a portion of the spectral image having the lowest received signal strength at the one or more wavelengths, it is possible to quantify the cosmetic residue present in other portions of the spectral image relative to the identified portion.

In embodiments, the analysis is performed in relation to a calibration image.

Performing the analysis in relation to a calibration image enables the skincare device to better determine a quantity of cosmetic residue present on the subject. In particular, such features enable the skincare device to identify cosmetic residue on the subject in situations in which the entirety of the subject is, to some extent, coated in cosmetic residue.

In embodiments, the controller is configured to capture the calibration image during a calibration procedure initiated by the user.

Performing the analysis in relation to a calibration image which is captured during a calibration procedure initiated by the user allows the skincare device to account for underlying variation in the subject (for example, due to variations in a user's skin condition) which might otherwise be erroneously attributed to the presence of cosmetic residue.

In embodiments, the calibration image is pre-stored in a memory on the device.

Performing the analysis in relation to a calibration image which is pre-stored in a memory on the device allows the skincare device to be calibrated during manufacture, such that it can operate without requiring the user to perform a calibration process.

In embodiments, the subject comprises a user's skin or a cosmetic bioplate.

Where the subject comprises a user's skin, the device can facilitate the provision of personalised skincare (i.e. skincare tailored to the specific skin conditions of the user). Where the subject comprises a cosmetic bioplate, the device can provide a repeatable means to quantify and compare the performance of cosmetic cleansers.

In embodiments, the action comprises adjusting one or more operating settings of the skincare device.

Adjusting one or more operating settings of the skincare device allows the skincare device to adjust its behaviour in response to the specific skin features detected in the user's skin. Thus, the skincare device may perform one or more additional assessments of the user's skin (for example, on the basis of sensor data associated with at least one different wavelength of light to those used in the spectral image) or might cause a remedial action to be taken (for example, by causing or instructing a modification to the user's skincare regimen).

In embodiments, the action comprises generating an alert. In such embodiments, it may be that the alert comprises one or more of: a visible alert, an audible alert, and a tactile alert.

By generating an alert, the skincare device can prompt the user to take an action in response to the determined measure of cosmetic residue, enabling the device to provide personalised skincare (i.e. skincare tailored to the specific skin conditions of the user).

In embodiments, the device comprises a light source configured to emit light onto the user's skin. In such embodiments, it may be that the action comprises controlling one or more parameters of light emission by the light source.

By incorporating a light source configured to emit light onto the user's skin, the skincare device is provided with the means to deliver a phototherapeutic treatment to the user's skin. Furthermore, controlling one or more parameters of light emission by the light source on the basis of the determined measure of cosmetic residue can allow the skincare device to use the light source to indicate a location on the user's skin of the cosmetic residue.

In embodiments, the action comprises providing an output to a user interface.

Providing an output to a user interface enables the skincare device to deliver feedback to the user on the determined measure of cosmetic residue (for example, by indicating a location on the subject of the cosmetic residue). Such feedback can prompt the user to take an action in response to the determined measure of cosmetic residue.

In embodiments, the subject comprises a user's face. In such embodiments, it may be that the output comprises an indication of a location on the user's face of the cosmetic residue.

Where the subject comprises a user's face and the output comprises an indication of a location on the user's face of the cosmetic residue, the skincare device can prompt the user to take an action in response to the determined measure of cosmetic residue (for example, to repeat cleansing of the indicated location).

In embodiments, the action comprises causing the user interface to display an image of a face highlighting the indicated location. In embodiments, the image comprises an image of the user's face. In embodiments, the image comprises a generic image of a user's face.

Where the image comprises an image of a face, the skincare device can easily indicate to the user the location on the user's face of the detected cosmetic residue.

In embodiments, the subject comprises a cosmetic bioplate. In such embodiments, it may be that the output comprises an indication of a location on the cosmetic bioplate of the cosmetic residue. In embodiments, the action comprises causing the user interface to display an image of the cosmetic bioplate highlighting the indicated location.

Where the subject comprises a cosmetic bioplate and the output comprises an indication of a location on the cosmetic bioplate of the cosmetic residue, the skincare device can prompt the user to take an action in response to the determined measure of cosmetic residue (for example, to repeat cleansing of the indicated location). Furthermore, where the subject comprises a plurality of cosmetic bioplates (for example, each of which having been cleaned using a different cleanser), the skincare device can indicate one or more of the cosmetic bioplates which have not been properly cleaned (for example, to allow a comparison of the different cleansers).

In embodiments, the skincare device comprises the user interface.

Providing the output to a user interface provided on the skincare device removes the need for any further computing devices to operate the skincare device.

In embodiments, the user interface is provided by a separate computing device. In such embodiments, it may be that providing the output comprises transmitting to the separate computing device a signal indicative of the output.

Providing the output on a separate computing device allows the user to interact with the skincare device using their existing devices (for example, the user's smartphone).

According to a second aspect of the present disclosure there is provided a method of operating a skincare device, the method comprising:

capturing a spectral image of a subject at one or more wavelengths outside of the visible spectrum; and analysing the spectral image to determine a measure of cosmetic residue present on the subject; and controlling the skincare device to perform an action associated with the determined measure of cosmetic residue.

According to a third aspect of the present disclosure there is provided a computer program comprising a set of instructions, which, when executed by a computerised device, cause the computerised device to perform a method of operating a skincare device, the method comprising:

capturing a spectral image of a subject at one or more wavelengths outside of the visible spectrum; and analysing the spectral image to determine a measure of cosmetic residue present on the subject; and controlling the skincare device to perform an action associated with the determined measure of cosmetic residue.

It will of course be appreciated that features described in relation to one aspect of the present disclosure may be incorporated into other aspects of the present disclosure. For example, a method of the disclosure may incorporate any of the features described with reference to an apparatus of the disclosure and vice versa.

DESCRIPTION OF THE DRAWINGS

Embodiments of the present disclosure will now be described by way of example only with reference to the accompanying schematic drawings of which:

FIGS. 5 to 15, 16a-c, 17a-b, 18 and 19 show flow charts illustrating the steps of methods according to embodiments of the present disclosure.

DETAILED DESCRIPTION

Figure 1:
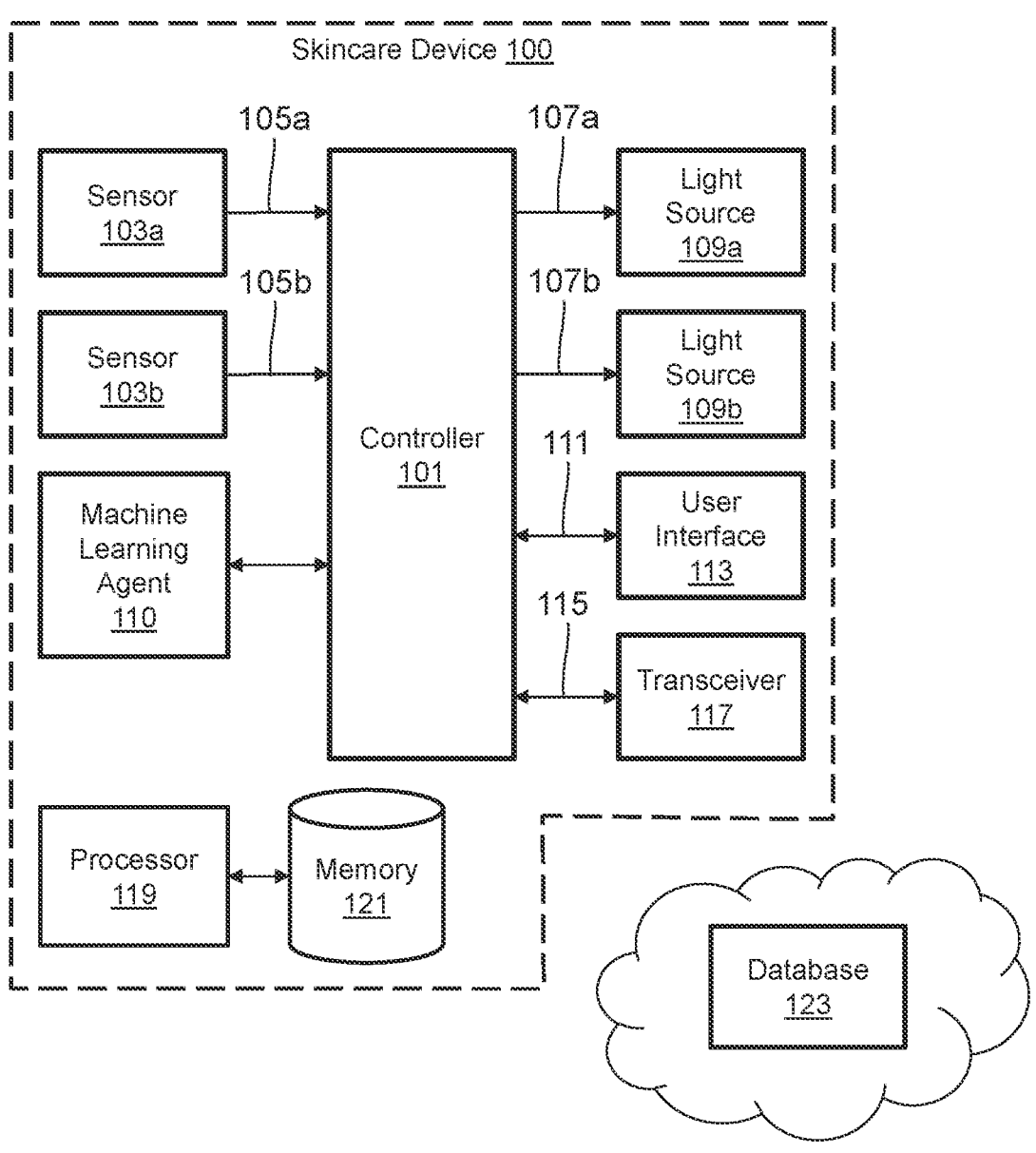
FIG. 1 shows a schematic view of a skincare device according to embodiments of the present disclosure.

FIG. 1 shows a schematic view of a skincare device 100 according to embodiments of the present disclosure.

Skincare device 100 comprises a controller 101. Controller 101 is operable to perform various data processing and/or control functions according to embodiments, as will be described in more detail below. Controller 101 may comprise one or more components. The one or more components may be implemented in hardware and/or software. The one or more components may be co-located or may be located remotely from each other in skincare device 100. Controller 101 may be embodied as one or more software functions and/or hardware modules. In embodiments, controller 101 comprises one or more processors configured to process instructions and/or data. Operations performed by the one or more processors may be carried out by hardware and/or software. Controller 101 may be used to implement the methods described herein. In embodiments, controller 101 is operable to output control signals for controlling one or more components of the skincare device 100.

Skin comprises a number of different metabolic constituents. Examples of such metabolic constituents include haemoglobin, collagen, elastin, melanin, sebum, and water. Each of these constituents interact differently with light. In particular, a given constituent may reflect light at a first wavelength, but absorb light at a second different wavelength, and may also emit light a third wavelength. The particular wavelengths of light reflected, absorbed, or emitted by that skin constituent are characterised by the reflectance characteristics of the constituent. Thus, the reflectance characteristics of a user's skin provide an indication of the particular metabolic constituents within that user's skin.

In embodiments, skincare device 100 comprises a sensor 103*a*. Sensor 103*a* is configured to sense one or more characteristics of the skin (for example, facial skin) of a user of device 100. In embodiments, sensor 103*a* is configured to detect light (for example, reflected from or emitted by the user's skin). The skilled person will appreciate that light, in this context, refers not only to visible light, but also to other non-visible frequencies of electromagnetic radiation. Thus, in embodiments, sensor 103*a* is configured to detect one or more (for example, all) of: visible light, near infra-red radiation, short-wave infra-red radiation, and ultra-violet light.

In embodiments, the one or more characteristics comprise reflectance characteristics. In embodiments, the one or more characteristics comprise a plurality of reflectance characteristics. In such embodiments, it may be that a first reflectance characteristic in the plurality is associated with a different wavelength of light to a second reflectance characteristic in the plurality. In embodiments, sensor 103*a* is configured to sense the one or more characteristics in a frequency band at least partly (for example, completely) outside of the visible spectrum. Sensors capable of detecting wavelengths of light corresponding to a frequency band outside of the visible spectrum are referred to herein as spectral sensors. In embodiments, sensor 103*a* is configured to sense the one or more characteristics in a frequency band at least partly (for example, completely) within the visible spectrum. Sensors capable of detecting wavelengths of light corresponding to a frequency band within the visible spectrum are referred to herein as visible light sensors. It will be understood that the visible spectrum refers to the range of wavelengths of light which are visible to the human eye. Specifically, the visible spectrum refers to light having a wavelength of between approximately 380 and 750 nanometres. It will be appreciated that a given sensor may comprise both a visible light sensor and a spectral sensor. Thus, in embodiments, sensor 103*a* is sensitive to wavelengths of light corresponding to frequency bands both within and outside of the visible spectrum.

In embodiments, sensor 103*a* is configured to output sensor data 105*a* indicating the one or more characteristics identified by sensor 103*a*. In embodiments, sensor data 105*a* indicates one or more wavelengths and/or intensities of light detected by sensor 103*a*. In such embodiments, it may be that controller 101 is configured to determine, on the basis of the wavelengths and/or intensities indicated by sensor data 105*a*, the one or more characteristics.

In embodiments, sensor 103*a* is configured to sense one or more characteristics of a first portion of the user's skin.

In such embodiments, it may be that, skincare device 100 comprises a further sensor 103*b*. In embodiments, sensor 103*b* is configured to sense one or more further characteristics of a further (for example, different) portion of the user's skin. Thus, in embodiments, sensors 103*a*, 103*b* are each configured to sense characteristics of distinct portions of the user's skin. In embodiments, the portion and the further portion are non-overlapping portions of the user's skin. In embodiments, the portion and the further portion each correspond to a different one of the user's: forehead, cheeks, chin, nose, and periocular area (each of which may be referred to as distinct "parts" of the user's face).

In embodiments, skincare device 100 comprises a plurality of sensors 103. In embodiments, skincare device 100 comprises at least three sensors, for example at least five sensors, at least ten sensors, or at least fifteen sensors. In such embodiments, it may be that each sensor in the plurality is configured to sense a respective portion of the user's skin. It may be that the portion sensed by at least one sensor in the plurality does not overlap the portions sensed by any of the remaining sensors in the plurality. It may be that the portion sensed by each sensor in the plurality does not overlap the portions sensed by any of the remaining sensors in the plurality.

In embodiments, sensors 103*a*, 103*b* are of the same type. Thus, in such cases, it may be that sensors 103*a*, 103*b* are both visible light sensors. Alternatively, it may be that sensors 103*a*, 103*b* are both spectral light sensors. In embodiments, sensors 103*a*, 103*b* are configured to sense corresponding characteristics of the portion and further portion respectively. In embodiments, sensors 103*a*, 103*b* are configured to detect the same wavelengths of light. In embodiments having more than two sensors, it may be that all sensors in the plurality are visible light sensors. Alternatively, it may be that all sensors in the plurality are spectral sensors. In embodiments, all sensors in the plurality are configured to detect substantially the same wavelengths of light.

In embodiments, skincare device 100 comprises a light source 109*a*. In embodiments, controller 101 is configured to generate control data 107*a*. Control data 107*a* is transmitted to light source 109*a*, and operates to control one or more parameters of light emission by light source 109*a*. Thus, controller 101 is configured to control one or more parameters of light emission by light source 109*a*. In embodiments, the one or more parameters comprise one or more of: a wavelength, an intensity, and a duration of light emission. In embodiments, the one or more parameters comprise an intensity of light emission at a specific wavelength.

In embodiments, skincare device 100 comprises a machine learning agent 110. In such embodiments, it may be that controller 101 is configured to control the one or more parameters on the basis of output from machine learning agent 110. In embodiments, machine learning agent 110 has been trained using a corpus of training users.

In embodiments, light source 109*a* comprises a plurality of light emitting diodes (LEDs). In such embodiments, it may be that at least one light emitting diode in the plurality is configured to emit light having a different wavelength to one or more other light emitting diodes in the plurality. In embodiments, controller 101 is configured to control light source 109*a* by controlling light emission by the plurality of light emitting diodes. In such embodiments, it may be that controller 101 is configured to control light emission by at least one light emitting diode in the plurality differently to one or more other light emitting diodes in the plurality. In embodiments, controller 101 is configured to control light emission by each light emitting diode in the plurality independently of the other light emitting diodes in the plurality. In embodiments, controller 101 is configured to control light source 109*a* to cause one or more light emitting diodes in the plurality (for example, light emitting diodes associated with a particular wavelength of light or configured to emit light onto a particular portion of the user's skin) to cease to emit light.

In embodiments, light source 109*a* comprises at least one variable wavelength light emitting diode. In such embodiments, it may be that controller 101 is configured to vary a wavelength of light emission by the at least one variable wavelength light emitting diode. It will be appreciated by the skilled person that light source 109*a* may comprise a plurality of light emitting diodes, one or more of which are variable wavelength light emitting diodes. Thus, controlling light source 109*a* may comprise both controlling light emission by the plurality of light emitting diodes and controlling a wavelength of light emission by a variable wavelength light emitting diode.

Phototherapy is a type of skincare treatment in which a user's skin is exposed to light in order to provide a cosmetic improvement to the user's skin. In embodiments, the one or more parameters are associated with a phototherapy treatment being undertaken by the user. Thus, in such embodiments, it may be that light source 109*a* is controlled by controller 101 to emit light for the purpose of delivering a phototherapeutic treatment to the user. It has been shown that exposing a user's skin to different wavelengths of light provides different cosmetic effects to the user's skin. Thus, in embodiments, light source 109*a* is controlled by controller 101 to emit light having wavelengths associated with a particular desired cosmetic effect.

In embodiments, light source 109*a* is configured to emit light onto a first portion of a user's skin (for example, substantially the same portion as is sensed by sensor 103*a*). In embodiments, skincare device 100 comprises a further light source 109*b*. Light source 109*b* is configured to emit light onto a second (for example, different) portion of the user's skin. In embodiments, the first portion and the second portion are non-overlapping portions of the user's face. In embodiments, the first portion and the second portion each correspond to a different one of the user's: forehead, cheeks, chin, nose, and periocular area.

In embodiments, controller 101 is configured to generate further control data 107*b*. Control data 107*b* is transmitted to further light source 109*b*, and operates to control one or more parameters of light emission by light source 109*b*. Thus, controller 101 is configured to control one or more parameters of light emission by light source 109*b*. In embodiments, the one or more one or more parameters comprise (as in the case of light source 109*a*) one or more of a wavelength, an intensity, and a duration of light emission. In embodiments, controlling the first light source and the second light source comprises causing at least one of the first light source and the second light source to cease to emit light.

In embodiments, skincare device 100 comprises one or more further light sources each configured to emit light onto a respective further portion of the user's skin. In such embodiments, controller 101 is configured to control each of the one or more further light sources to emit light having one or more respective parameters onto the respective portion. In such embodiments, it may be that skincare device 100 comprises multiple light sources configured to emit light onto one of the user's: forehead, cheeks, chin, nose, and periocular area. In embodiments, skincare device 100 comprises multiple light sources configured to emit light onto each of the user's: forehead, cheeks, chin, nose, and periocular area. In embodiments, skincare device 100 comprises at least three light sources, for example at least five light sources, at least ten light sources, or at least fifteen light sources. In such embodiments, it may be that each light source in the plurality is configured to illuminate a respective portion of the user's skin.

In embodiments, controller 101 is configured to control the one or more parameters such that light emission onto the first portion differs from light emission onto the second portion. In embodiments having more than two light sources, it may be that controller 101 is configured to control the one or more parameters such that light emission onto a first portion of the user's skin differs from light emission onto one or more (for example, all) of the other portions. In such embodiments, it may be that controller 101 is configured to control the one or more parameters such that light emission onto each of the portions differs from light emission onto one or more (for example, all) of the other portions.

In embodiments, skincare device 100 comprises a user interface 113. In embodiments, user interface 113 comprises a display. In such embodiments, it may be that controller 101 is configured to generate display data 111 configured to control the display (for example, to display feedback to the user).

In embodiments, user interface 113 is configured to receive an indication of configuration data for using in controlling the operation of skincare device 100 (for example, an indication of one or more parameters for use by controller 101 in controlling light sources 109). In embodiments, controller 101 is configured to control light sources 109 in response to receipt of the indication. In embodiments, the indication is received by user input (either directly to the device or received via a separate computing device).

In embodiments, user interface 113 is configured to receive user input (for example, indicating configuration data for skincare device 100). Thus, the indication may be received by user interacting with user interface 113. In embodiments where the user interface comprises a display, it may be that the display comprises a touch screen. In such embodiments, it may be that the skincare device 100 is configured to receive user input by the user touching the touch screen. In embodiments, user interface 113 comprises a microphone. In such embodiments, it may be that skincare device 100 is configured to receive user input in the form of a spoken command by the user. In embodiments, user interface 113 comprises one or more buttons. In such embodiments, it may be that skincare device 100 is configured to receive user input by the user pressing at least one of the one or more buttons.

In embodiments, skincare device 100 comprises a transceiver 117, which is configured to exchange transceiver data 115 with controller 101. Transceiver 117 is configured to communicate with one or more other computing devices via a communications network. In embodiments, the transceiver is configured to communicate wirelessly with the one or more other computing devices. In such embodiments, skincare device 100 may comprise an antenna. In alternative embodiments, the transceiver is configured to communicate with the one or more other computing devices via a wired communication network. In embodiments, the indication (of configuration data) is received (for example, by transceiver 117) via a signal transmitted over a communications network. In such embodiments, it may be that the signal is transmitted in response to receipt of user input on a separate computing device. Examples of such separate computing devices include personal computers (for example, a laptop computer or a tablet computer), smartphones, or a dedicated user input device associated with skincare device 100.

In embodiments, skincare device 100 is configured to communicate with a database 123 (for example, to access data held within database 123). In such embodiments, it may be that skincare device 100 is configured to communicate with database 123 by use of transceiver 117.

Figure 2:
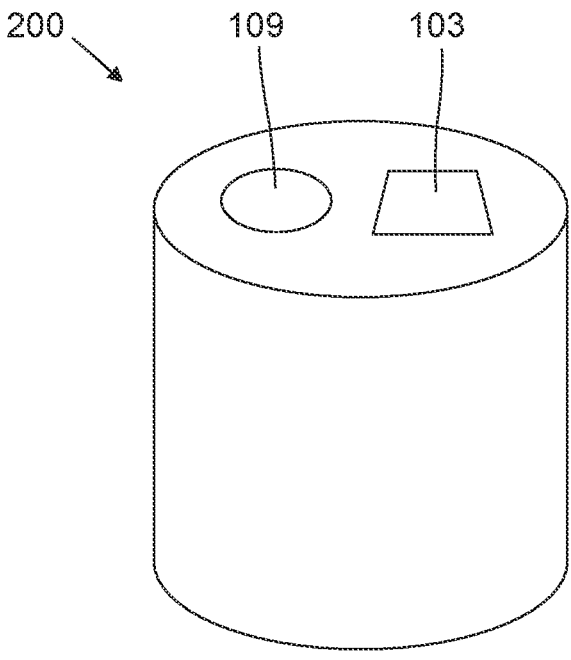
FIGS. 2 to 4 show perspective views of a skincare devices according to embodiments of the present disclosure.

In embodiments, skincare device 100 comprises a handheld device. FIG. 2 shows a perspective view of a handheld device 200 according to embodiments of the present disclosure. In the particular embodiments illustrated, handheld device 200 comprises only a single sensor 103 and light source 109. However, it will be appreciated that, in other embodiments, handheld device 200 may comprise one or more further sensors and/or light sources.

Figure 3:
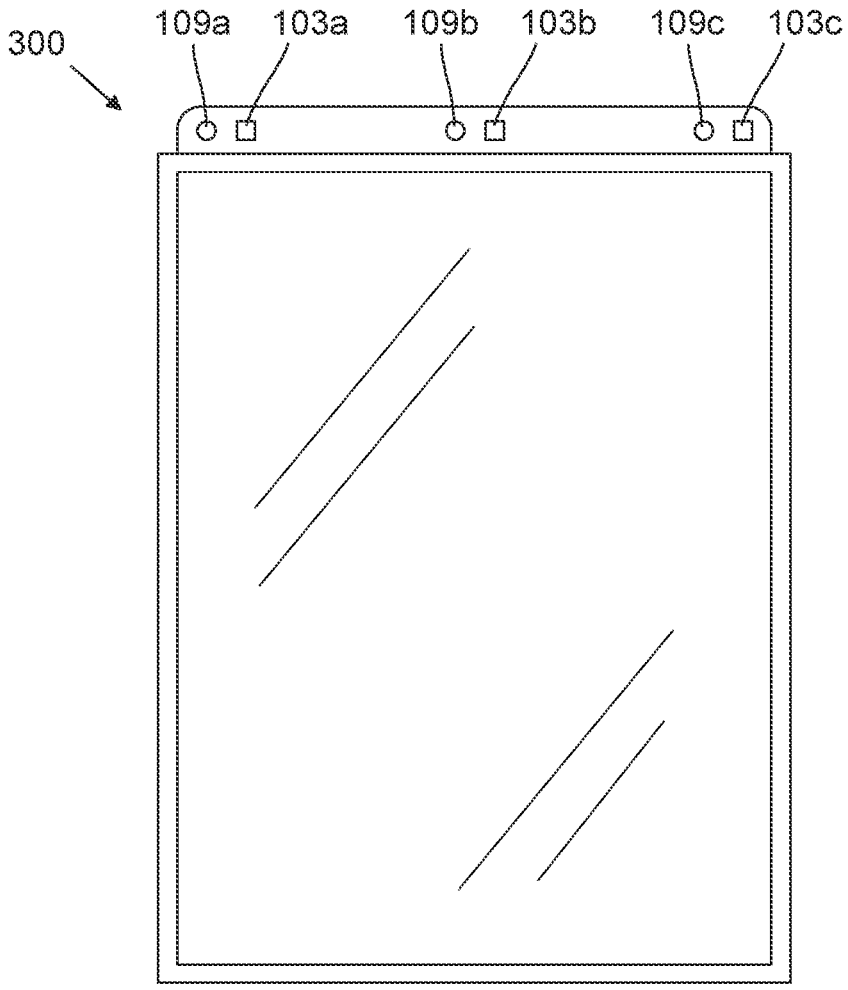

In embodiments, skincare device 100 comprises a mirror (for example a vanity mirror). FIG. 3 shows a perspective view of a mirror 300 according to embodiments of the present disclosure. In the particular embodiments illustrated, mirror 300 comprises three sensors 103a, 103b, 103c and three light sources 109a, 109b, 109c. However, it will be appreciated that, in other embodiments, mirror 300 may comprise other numbers of sensors and/or light sources. In this particular illustrated embodiment, sensors 103a, 103b, 103c and light sources 109a, 109b, 109c are positioned around an outer frame of mirror 300 in pairs, such that each sensor is positioned in close proximity to one of the light sources. In this case, sensors 103a, 103b, 103c and light sources 109a, 109b, 109c are arranged along a top edge of mirror 300. It will be appreciated that, in other embodiments, the sensors and light sources may be arranged along one or more (for example, all) different edges of mirror 300.

Figure 4:
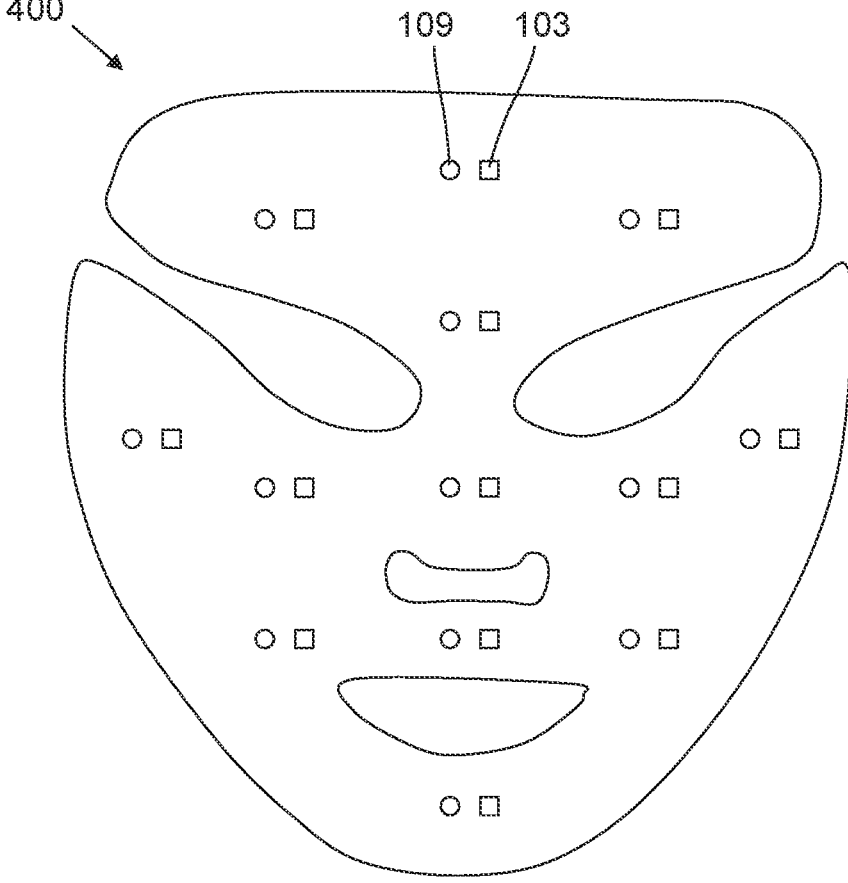

In embodiments, skincare device 100 comprises a face mask. FIG. 4 shows a perspective view of a face mask 400 according to embodiments of the present disclosure. In the particular embodiments illustrated, face mask 400 comprises a large number of sensors 103 and light sources 109 (in this particular example, thirteen of each). However, it will be appreciated that, in other embodiments, face mask 400 may comprise other numbers of sensors and/or light sources. In embodiments, all of sensors 103 and light sources 109 are located on an interior surface of the face mask (i.e. the surface of the face mask which, in use, is proximal to the user's skin).

It will be appreciated by the skilled person that, in other embodiments, the skincare device may comprise other form factors not specifically listed above. For example, the skincare device may comprise a desk lamp, a floor lamp, or a purpose-built scanner unit.

In embodiments, the skincare device 100 comprises a processor 119 and an associated memory 121. In such embodiments, it may be that some or all of the functionality of controller 101, sensors 103, light sources 109, user interface 113, and transceiver 117 is implemented partially or wholly by processor 119 (for example, by executing instructions stored in the memory 121). In embodiments, processor 119 and memory 121 comprise part of controller 101.

In embodiments, sensor 103a is configured to sense one or more characteristics of a user's skin. In such embodiments, sensor 103a may be configured to generate sensor data 105a associated with the sensed one or more characteristics. In embodiments, controller 101 is configured to receive sensor data 105a and, on the basis of sensor data 105a (i.e. on the basis of the sensed one or more characteristics), determine a skin state associated with the user's skin. It will be appreciated by the skilled person that a skin state characterises one or more aspects of the condition of the user's skin. For example, a skin state may characterise a degree of dryness or elasticity of the user's skin. In embodiments, the determined skin state is associated with one or more of: skin age, skin moisture level, skin oil level, skin elasticity, skin fat content, skin protein content, skin oxygenation levels, skin topography, skin roughness, skin colour, skin tone, and skin gloss. Determining a skin state of the user's skin can allow skincare device 100 to identify one or more remedial actions to be taken, either directly by skincare device 100 or by the user, in order to initiate a desired change in the condition of the user's skin.

In embodiments, controller 101 is further configured to generate control data 107a on the basis of the determined skin state. Thus, controller 101 may be configured to control (for example, by generating appropriate control data 107a) one or more parameters of light emission by light source 109a on the basis of the determined skin state. Thus, in such embodiments, skincare device 100 can identify a phototherapeutic treatment for the specific user of skincare device 100, and deliver the identified phototherapeutic treatment to the user.

As mentioned above, in embodiments, skincare device 100 comprises a first sensor 103a, configured to sense one or more characteristics of a first portion of a user's skin, and a second sensor 103b, configured to sense one or more further characteristics of a different further portion of the user's skin. In such embodiments, it may be that controller 101 is configured to determine a skin state associated with the first portion of the user's skin. In embodiments, controller 101 is configured to, on the basis of the sensed one or more further characteristics, determine a further skin state associated with the further portion of the user's skin. Thus, in embodiments, skincare device 100 is configured to separately analyse multiple distinct portions of a user's skin. In embodiments in which skincare device 100 comprises more than two sensors 103, it may be that each of the sensors 103 is configured to sense one or more characteristics of a respective distinct portion of the user's skin. In such embodiments, it may be that controller 101 is configured to determine a respective skin state skin state associated with each of the respective portions.

In such embodiments, it may be that controller 101 is configured to control the one or more parameters of light emission on the basis of the skin state and the further skin state. In such embodiments, it may be that controller 101 is configured to generate control data 107b on the basis of the determined further skin state. Thus, controller 101 may be configured to control (for example, by generating appropriate control data 107b) one or more parameters of light emission by light source 109b on the basis of the determined further skin state. In embodiments, controller 101 is configured to generate control data 107a, 107b to control light sources 109a, 109b to each emit light having different parameters. Thus, in embodiments, controller 101 is configured to control the one or more parameters such that light emission onto the first portion differs from light emission onto the second portion (for example, to deliver differing phototherapeutic treatments to different parts of the user's skin). In embodiments in which skincare device 100 comprises more than two light sources 109, it may be that each of the light sources 109 is configured to emit light onto a distinct portion of the user's skin. In such embodiments, it may be that controller 101 is configured to control each of the light sources 109 to emit light having characteristics which differ from those of one or more of the other light sources.

FIG. 5 shows a flow chart illustrating the steps of a method 500 of controlling a skincare device according to embodiments of the present disclosure.

A first step of method 500, represented by item 501, comprises sensing one or more characteristics of a user's skin.

In embodiments, the one or more characteristics comprise reflectance characteristics. In embodiments, the one or more characteristics comprise a plurality of reflectance characteristics. In such embodiments, it may be that a first reflectance characteristic in the plurality is associated with a different wavelength of light to a second reflectance characteristic in the plurality. In embodiments, the sensing is performed using a frequency band outside of the visible spectrum.

A second step of method 500, represented by item 503, comprises controlling a light source to emit light onto the user's skin. In embodiments, the light source is part of the skincare device. In alternative embodiments, the light source is separate from the skincare device.

A third step of method 500, represented by item 505, comprises, on the basis of the sensed one or more characteristics, determining a skin state associated with the user's skin.

In embodiments, the sensing is of a first portion of the user's skin. In such embodiments, method 500 may comprise an optional fourth step, represented by item 507, of sensing one or more further characteristics of a different further portion of the user's skin.

In such cases, method 500 may also comprise an optional fifth step, represented by item 509, of determining a skin state associated with the first portion of the user's skin and, on the basis of the sensed one or more further characteristics, determine a further skin state associated with the further portion of the user's skin.

A sixth step of method 500, represented by item 511, comprises, on the basis of the determined skin state, controlling one or more parameters of light emission by the light source.

In embodiments, the one or more parameters comprise one or more of: a wavelength, an intensity, and a duration of light emission. In embodiments, the one or more parameters are associated with a phototherapy treatment being undertaken by the user.

In embodiments, the controlling is performed on the basis of the skin state and the further skin state. In embodiments, the controlling comprises controlling the one or more parameters such that light emission onto the first portion differs from light emission onto the second portion. In such embodiments, it may be that the portion and the further portion are non-overlapping portions of the user's face. In embodiments, the portion and the further portion each correspond to a different one of the user's forehead, cheeks, chin, nose, and periocular area. In embodiments, the controlling comprises operating a machine learning agent, the machine learning agent having been trained using a corpus of training users (for example, as is described in further detail below).

It will be appreciated that method 500 may be implemented by a computer program comprising a set of instructions, which, when executed by a computerised device, cause the computerised device to perform method 500.

In embodiments, skincare device 100 includes a first light source 109a, configured to emit light onto a first portion of a user's skin, and a second light source 109b, configured to emit light onto a second portion of the user's skin. In embodiments, controller 101 is configured to control light source 109a (for example, by generating appropriate control data 107a) to emit light having one or more first parameters onto the first portion. In embodiments, controller 101 is further configured to control light source 109b (for example, by generating appropriate control data 107b) to emit light having one or more second different parameters onto the second portion. In embodiments, controller 101 is configured to generate control data 107a, 107b to control light sources 109a, 109b to each emit light having different parameters. Thus, in embodiments, controller 101 is configured to control light sources 109a, 109b such that light emission onto the first portion differs from light emission onto the second portion. In embodiments, skincare device 100 comprises one or more further light sources. In such embodiments, controller 101 may be configured to control each of the one or more further light sources independently (for example, such that each light source emits light having a different one or more parameters to the other light sources).

It may be that the first portion and second portion each relate to different parts of the user's skin (for example, different ones of the user's forehead, cheeks, chin, nose, and periocular area). Alternatively, the first portion and second portion each relate to the same part of the user's skin (for example, one of the user's forehead, cheeks, chin, nose, and periocular area). In embodiments having more than two light sources, it may be that at least one (for example, each) of the light sources is configured to emit light onto a different part of the user's face to one or more (for example, all) of the other light sources. In embodiments having more than two light sources, it may be that at least two of the light sources are configured to emit light onto the same part of the user's face.

In embodiments, light emission by light sources 109a, 109b (and optionally any further light sources) is associated with a phototherapeutic treatment being undertaken by the user. Thus, in embodiments, controller 101 is configured to generate control data 107a, 107b in order to vary one or more of a wavelength, an intensity, and a duration of light emission by light sources 109a, 109b in order to deliver a phototherapeutic treatment to the user's skin. In embodiments, controlling the light sources 109a, 109b comprises causing at least one of light sources 109a, 109b to cease to emit light.

In embodiments, controller 101 is configured to generate control data 107a, 107b on the basis of a received indication of one or more first parameters and one or more second parameters (for example, for use in controlling light sources 109a, 109b). In embodiments, such indications may be received from a separate computing device (for example, via transceiver 117). In such embodiments, it may be that the indication was generated and transmitted in response to user input on the separate computing device.

FIG. 6 shows a flow chart illustrating the steps of a method 600 of controlling a skincare device according to embodiments of the present disclosure.

An optional first step of method 600, represented by item 601, comprises receiving an indication of one or more first parameters and one or more second parameters. In embodiments, the indication is received via a signal transmitted over a communications network. In such embodiments, it may be that the signal is transmitted in response to receipt of user input on a separate computing device. In embodiments, the indication is received by user input to the device by one or more of: pressing a button, and providing a spoken command.

A second step of method 600, represented by item 603, comprises controlling a first light source to emit light having one or more first parameters onto a first portion of a user's skin. In embodiments, the controlling of the first light source is performed in response to receipt of the one or more first parameters.

A third step of method 600, represented by item 605, comprises controlling a second light source to emit light having one or more second different parameters onto a second portion of the user's skin. In embodiments, the controlling of the first light source is performed in response to receipt of the one or more first parameters.

In embodiments, the first portion and the second portion are non-overlapping portions of the user's face. In embodiments, the first portion and the second portion each correspond to a different one of the user's: forehead, cheeks, chin, nose, and periocular area.

In embodiments, the one or more first parameters and the one or more second parameters each comprise one or more of: a wavelength, an intensity, and a duration of light emission. In embodiments, controlling the first light source and the second light source comprises causing at least one of the first light source and the second light source to cease to emit light.

An optional fourth step of method 600, represented by item 607, comprises controlling one or more further light sources, each configured to emit light onto a respective further portion of the user's skin, to emit light having one or more respective parameters onto the respective portion.

In embodiments, the device comprises multiple light sources configured to emit light onto one of the user's: forehead, cheeks, chin, nose, and periocular area. In embodiments, the device comprises a face mask. In such embodiments, the first light source and the second light source are each located on an interior surface of the face mask.

It will be appreciated that method 600 may be implemented by a computer program comprising a set of instructions, which, when executed by a computerised device, cause the computerised device to perform method 600.

In embodiments, sensor 103a is configured to sense one or more characteristics of a photosensitive substance, rather than (or in addition to) a user's skin. In such embodiments, it may be that the photosensitive substance is configured to change characteristics in response to exposure to light (for example, light associated with a phototherapeutic treatment). In embodiments, the one or more characteristics comprise reflectance characteristics. In embodiments, the photosensitive substance may be configured to change colour. In embodiments, the change in reflectance characteristics is associated with one or more wavelengths of light within the visible spectrum (for example, where the photosensitive substance is configured to change colour). In such embodiments, it may be that the change in reflectance characteristics is visible to the human eye. Alternatively or additionally, the change in reflectance characteristics may be associated with one or more wavelengths of light outside of the visible spectrum. Thus, in embodiments, the change in reflectance characteristics may not be visible to the human eye. In embodiments, the photosensitive substance is further configured to facilitate the transmission of one or more wavelengths of light (for example, one or more wavelengths of light associated with a phototherapeutic treatment being undertaken by the user) to the user's skin.

In such embodiments, it may be that controller 101 is configured to monitor the sensed one or more characteristics of the photosensitive substance applied to the user's skin (for example, by periodically sensing the one or more characteristics). In embodiments, controller 101 is configured to, in response to the monitoring indicating a change in the one or more characteristics, control one or more parameters of light emission by light source 109a. For example, it may be that controller 101 is configured to, in response to the monitoring indicating a change in the one or more characteristics (which may, for example, be associated with completion of a phototherapeutic treatment being undertaken by the user), control light source 109a to cease emitting light.

In embodiments, sensor 103a is configured to sense one or more characteristics of photosensitive substance applied to a first portion of the user's skin. In embodiments, skincare device 100 comprises a further sensor 103b configured to sense one or more second characteristics of photosensitive substance applied to a second portion of the user's skin. In such embodiments, it may be that controller 101 is configured to monitor the sensed one or more characteristics and the sensed one or more second characteristics. In embodiments, controller 101 is configured to control the one or more parameters in response to the monitoring indicating a change in the one or more characteristics or the one or more second characteristics. For example, it may be that controller 101 is configured to, in response to the monitoring indicating a change in the one or more characteristics or the one or more second characteristics (which may, for example, be associated with completion of a phototherapeutic treatment being undertaken by the user), control light source 109a to cease emitting light.

Where skincare device 100 comprises multiple light sources configured to emit light onto different portions of the user's skin, it may be that controller 101 is configured to, in response to the monitoring indicating a change in the one or more characteristics of a portion of the photosensitive substance, control only the light sources associated with that portion to cease to emit light. In embodiments, skincare device 100 is configured to emit light onto a portion of photosensitive substance only until the monitoring indicates a change in the one or more characteristics of that portion.

FIG. 7 shows a flow chart illustrating the steps of a method 700 of controlling a skincare device according to embodiments of the present disclosure.

A first step of method 700, represented by item 701, comprises controlling a light source configured to emit light onto a user's skin.

A second step of method 700, represented by item 703, comprises sensing one or more characteristics of a photosensitive substance, wherein the photosensitive substance is configured to change characteristics in response to exposure to light. In embodiments, the one or more characteristics comprise reflectance characteristics.

A third step of method 700, represented by item 705, comprises monitoring the sensed one or more characteristics of the photosensitive substance applied to the user's skin.

In embodiments, the sensing is of photosensitive substance applied to a first portion of the user's skin. In such embodiments, method 700 may comprise an optional fourth step, represented by item 707, of sensing one or more second characteristics of photosensitive substance applied to a second portion of the user's skin.

An optional fifth step of method 700, represented by item 709, comprises monitoring the sensed one or more second characteristics of the photosensitive substance applied to the second portion of the user's skin.

A sixth step of method 700, represented by item 711, comprises, in response to the monitoring indicating a change in the one or more characteristics, controlling one or more parameters of light emission by the light source. In embodiments, the one or more parameters comprise one or more of: a wavelength, an intensity, and a duration of light emission. In embodiments, the one or more parameters are associated with a phototherapy treatment being undertaken by the user. In embodiments, the controlling comprises operating a machine learning agent, the machine learning agent having been trained using a corpus of training users (for example, as is described in further detail below). In embodiments including optional steps 709 and 711, the controlling may be performed in response to the monitoring indicating a change in either or both of the one or more characteristics and the one or more second characteristics. In embodiments, the controlling comprises controlling the one or more parameters such that light emission onto the first portion differs from light emission onto the second portion.

In embodiments, the portion and the further portion are non-overlapping portions of the user's face. In embodiments, the first portion and the second portion each correspond to a different one of the user's: forehead, cheeks, chin, nose, and periocular area.

It will be appreciated that method 700 may be implemented by a computer program comprising a set of instructions, which, when executed by a computerised device, cause the computerised device to perform method 700.

Embodiments of the present disclosure provide a use of a photosensitive substance to indicate the progress of a cosmetic phototherapy treatment.

In embodiments, the photosensitive substance is sensitive to one or more wavelengths of light used in the cosmetic phototherapy treatment. In such embodiments, it may be that the photosensitive substance is configured to change colour in response to exposure to the one or more wavelengths of light.

In embodiments, sensor 103*a* comprises a spectral sensor configured to sense, at a frequency band outside of the visible spectrum, one or more characteristics of a user's skin. In embodiments, controller 101 is configured to, on the basis of the sensed one or more characteristics, identify one or more metabolic constituents of the user's skin. In embodiments, the one or more metabolic constituents comprise one or more of: haemoglobin, collagen, elastin, melanin, and water.

In embodiments, sensor 103*a* is also configured to sense one or more further characteristics of the user's skin. In such embodiments, it may be that sensor 103*a* is configured to sense the one or more further characteristics at a frequency band at least partly within in the visible spectrum. As mentioned previously, in embodiments, the one or more characteristics comprise reflectance characteristics. In embodiments, the one or more further characteristics also comprise reflectance characteristics. In embodiments in which sensor 103*a* is configured to sense one or more further characteristics of the user's skin, it may be that controller 101 is configured to determine, on the basis of the sensed one or more further characteristics, topological features associated with the user's skin. It will be understood by the skilled person that topological features refer to features of the shape and/or texture of the surface of the user's skin.

In embodiments, controller 101 is configured to determine one or more skin features associated with the identified one or more constituents In embodiments, in which sensor 103*a* is configured to sense one or more further characteristics of the user's skin and controller 101 is configured to determine topological features associated with the user's skin, it may be that controller 101 is configured to determine the one or more skin features on the basis of both the identified metabolic constituents and topological features. In embodiments, the determined one or more skin features comprise one or more of: passive skin wrinkles, active skin wrinkles, and precursors thereto.

In embodiments, controller 101 is configured to process the sensed one or more further characteristics to generate an image of the user's skin. In other embodiments, it may be that sensor 103*a* is configured to generate the image. In embodiments, controller 101 may be configured to determine the topological features by performing texture based image processing on the generated image. Such image processing techniques are known in the art and will not be discussed further here.

In embodiments, controller 101 is configured to control the skincare device to perform an action associated with the determined one or more skin features. In embodiments, the action may comprise adjusting one or more operating settings of skincare device 100. For example, the action may comprise adjusting one or more operating settings to cause skincare device 100 to perform one or more further analyses of the user's skin. In embodiments in which skincare device 100 comprises light source 109*a*, the action may comprise controlling one or more parameters of light emission by light source 109*a* (for example, to provide a cosmetic phototherapeutic treatment to the user).

In embodiments, the action comprises generating an alert. In such embodiments, it may be that the alert comprises a visible alert (for example, displayed on the display of user interface 113). In embodiments, the alert comprises an audible alert (for example, causing skincare device 100 to generate a sound). In embodiments, the alert comprises a tactile alert (for example, causing skincare device 100 to vibrate).

In embodiments, the action comprises providing an output to a user interface (for example, user interface 113). In embodiments, the user interface is provided by a separate computing device. In such embodiments, providing the output may comprise transmitting (for example, by transceiver 117) to the separate computing device a signal indicative of the output.

In embodiments, controller 101 is configured to determine the one or more skin features by operating a classifier (i.e. a classification algorithm). In such embodiments, it may be that the classifier has been trained using spectral sensor training data comprising characteristics of a corpus of training users' skin and indications of known skin features of the corpus of training users. In embodiments, the classifier comprises a machine learning agent.

FIG. 8 shows a flow chart illustrating the steps of a method 800 of controlling a skincare device according to embodiments of the present disclosure.

A first step of method 800, represented by item 801, comprises sensing at a frequency band outside of the visible spectrum, one or more characteristics of a user's skin. In embodiments, the one or more characteristics comprise reflectance characteristics. In embodiments, the one or more characteristics comprise a plurality of reflectance characteristics. In such embodiments, it may be that a first reflectance characteristic in the plurality is associated with a different wavelength of light to a second reflectance characteristic in the plurality.

A second step of method 800, represented by item 803, comprises, on the basis of the sensed one or more characteristics, identifying one or more metabolic constituents of the user's skin. In embodiments, the one or more metabolic constituents comprise one or more of: haemoglobin, collagen, elastin, melanin, and water.

An optional third step of method 800, represented by item 805, comprises sensing one or more further characteristics of the user's skin. In embodiments, the sensing is performed at a frequency band at least partly within in the visible spectrum.

An optional fourth step of method 800, represented by item 807, comprises processing the sensed one or more further characteristics to generate an image of the user's skin.

An optional fifth step of method 800, represented by item 809, comprises determining on the basis of the sensed one or more further characteristics, topological features associated with the user's skin. In embodiments comprising the fourth step 807, it may be that the determining comprises performing texture based image processing on the generated image.

A sixth step of method 800, represented by item 811, comprises determining one or more skin features associated with the identified one or more constituents. In embodiments, the identified one or more skin features comprise one or more of: passive skin wrinkles, active skin wrinkles, and precursors thereto. In embodiments comprising the third step 805 and fifth step 809, it may be that the one or more skin features are further determined on the basis of the topological features. In embodiments, determining the one or more skin features comprises operating a classifier (e.g. a classification algorithm). In embodiments, the classifier has been trained using spectral sensor training data comprising characteristics of a corpus of training users' skin and indications of known skin features of the corpus of training users. In embodiments, the classifier comprises a machine learning agent.

A seventh step of method 800, represented by item 813, comprises controlling the skincare device to perform an action associated with the determined one or more skin features. In embodiments, the action comprises adjusting one or more operating settings of the skincare device. In embodiments, the action comprises generating an alert. In such embodiments, it may be that the alert comprises one or more of: a visible alert, an audible alert, and a tactile alert. In embodiments, the skincare device comprises a light source configured to emit light onto the user's skin and the action comprises controlling one or more parameters of light emission by the light source. In embodiments, the action comprises providing an output to a user interface. In such embodiments, it may be that the skincare device comprises the user interface. In alternative embodiments, it may be that the user interface is provided by a separate computing device. In such embodiments, it may be that the action comprises transmitting to the separate computing device a signal indicative of the output.

It will be appreciated that method 800 may be implemented by a computer program comprising a set of instructions, which, when executed by a computerised device, cause the computerised device to perform method 800.

In embodiments, sensor 103a is configured to sense intensities of light produced at a plurality of wavelengths by interaction of light with the user's skin. The light may originate from light source 109a and/or from external light sources. Thus, in embodiments, the light includes one or both of light emitted by light source 109a and ambient light. In embodiments, the interaction comprises one or more of: reflection from the user's skin, absorption by the user's skin, and emission by the user's skin. In embodiments, the plurality of wavelengths comprise wavelengths associated with a frequency band outside of the visible spectrum.

In such embodiments, it may be that controller 101 is configured to, on the basis of the sensed intensities, identify at least one wavelength of light for which the sensed intensity is outside of a predetermined intensity range. In embodiments, the predetermined intensity range may depend on the particular wavelength of light in question. Thus, it may be that a first wavelength of light is associated with a first predetermined intensity range and a second wavelength of light is associated with a second different predetermined intensity range. In embodiments, the identified at least one wavelength of light comprises one or more wavelengths of light outside of the visible spectrum. In embodiments, the identified at least one wavelength of light comprises only wavelengths of light outside of the visible spectrum.

In embodiments, controller 101 is configured to control light source 109a to modify light emission at the identified at least one wavelength. In embodiments, modifying light emission comprises adjusting the intensity of light emission at the identified at least one wavelength. In embodiments, controller 101 is configured to, in response to the sensed intensity being above an upper limit of the predetermined intensity range, modify light emission to reduce the intensity of light emission at the identified at least one wavelength. In embodiments, controller 101 is configured to, in response to the sensed intensity being below a lower limit of the predetermined intensity range, modify light emission to increase the intensity of light emission at the identified at least one wavelength. Thus, in embodiments, controller 101 is configured to control light source 109a to attempt to bring the sensed light intensity within the predetermined intensity range. It will be appreciated that whether or not a given intensity range can be brought within the predetermined intensity range is not entirely within the control of skincare device 100, as other nearby light sources not under the control of controller 101 may also emit light onto the user's skin.

As discussed above, in embodiments, light source 109a comprises a plurality of light emitting diodes. In such embodiments, it may be that at least one light emitting diode in the plurality is configured to emit light having a different wavelength to one or more other light emitting diodes in the plurality. In embodiments, controller 101 is configured to control light source 109a by controlling light emission by the plurality of light emitting diodes. In embodiments, controller 101 is configured to control an intensity of light emission by one or more light emitting diodes in the plurality. In embodiments, controller 101 is configured to, in response to the sensed intensity being above an upper limit of the predetermined intensity range, control one or more of the plurality of diodes (for example, one or more diodes corresponding to the identified at least one wavelength) to reduce an intensity of light emission. In embodiments, controller 101 is configured to, in response to the sensed intensity being below a lower limit of the predetermined intensity range, control one or more of the plurality of diodes (for example, one or more diodes corresponding to the identified at least one wavelength) to increase an intensity of light emission. In embodiments, it may be that controller 101 is configured to control light source 109a to decrease an intensity of light emission by causing one or more of the plurality of light emitting diodes to cease to emit light. In embodiments, it may be that controller 101 is configured to control light source 109a to increase an intensity of light emission by causing one or more of the plurality of light emitting diodes not presently emitting light to start to emit light.

Figure 9:
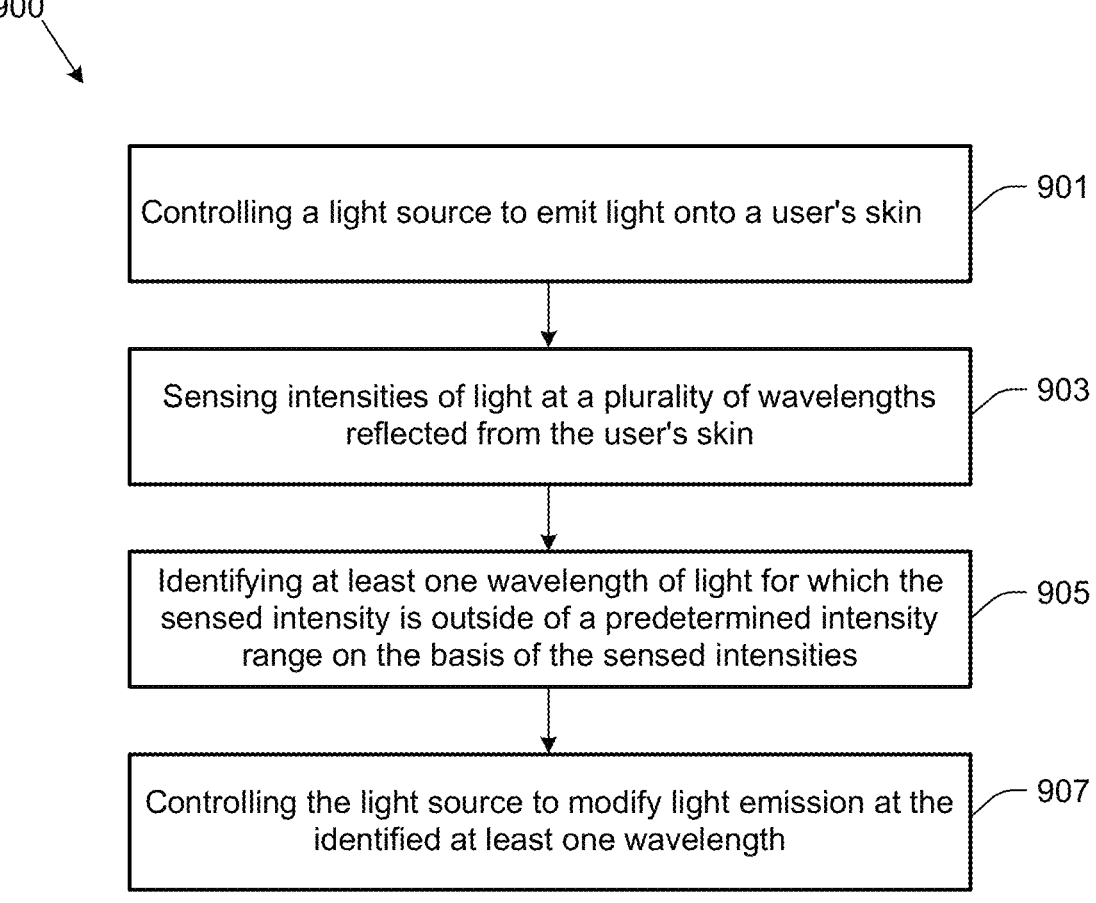

FIG. 9 shows a flow chart illustrating the steps of a method 900 of controlling a skincare device according to embodiments of the present disclosure.

A first step of method 900, represented by item 901, comprises controlling a light source to emit light onto a user's skin.

A second step of method 900, represented by item 903, comprises sensing intensities of light at a plurality of wavelengths reflected from the user's skin. In embodiments, the plurality of wavelengths comprise wavelengths associated with a frequency band outside of the visible spectrum. In embodiments, the light includes light emitted one or both of light emitted by light source 109a and ambient light. In embodiments, the interaction comprises one or more of: reflection from the user's skin, absorption by the user's skin, and emission by the user's skin.

A third step of method 900, represented by item 905, comprises on the basis of the sensed intensities, identifying at least one wavelength of light for which the sensed intensity is outside of a predetermined intensity range.

A fourth step of method 900, represented by item 907, comprises controlling the light source to modify light emission at the identified at least one wavelength. In embodiments, modifying light emission comprises adjusting the intensity of light emission at the identified at least one wavelength. In embodiments, the modifying comprises, in response to the sensed intensity being above an upper limit of the predetermined intensity range, reducing the intensity of light emission at the identified at least one wavelength. In embodiments, the modifying comprises, in response to the sensed intensity being below a lower limit of the predetermined intensity range, increasing the intensity of light emission at the identified at least one wavelength.

In embodiments, the light source comprises a plurality of light emitting diodes. In such embodiments, it may be that at least one light emitting diode in the plurality is configured to emit light having a different wavelength to one or more other light emitting diodes in the plurality. Thus, in embodiments, controlling the light source comprises controlling light emission by the plurality of light emitting diodes. In embodiments, controlling the light source comprises controlling light emission by at least one light emitting diode in the plurality differently to the one or more other light emitting diodes in the plurality. In embodiments, controlling the light source comprises controlling each light emitting diode in the plurality independently of the other light emitting diodes in the plurality. In embodiments, the light source comprises at least one variable wavelength light emitting diode. In such embodiments, it may be that controlling the light source comprises varying a wavelength of light emission by the at least one variable wavelength light emitting diode.

It will be appreciated that method 900 may be implemented by a computer program comprising a set of instructions, which, when executed by a computerised device, cause the computerised device to perform method 900.

In embodiments, controller 101 is configured to receive an indication of one or more skin constituents for which the user's skin is to be scanned. In embodiments, the indication of the one or more constituents is associated with a skin feature. Thus, in embodiments, controller 101 is configured to receive an indication of a skin feature for which the user's skin is to be scanned. In embodiments, controller 101 is configured to receive the indication by retrieving from a memory (for example, memory 121) a predetermined list of skin constituents to be scanned. In embodiments, the indication is received via a signal transmitted over a communications network (for example, via transceiver 117). In such embodiments, it may be that the signal is transmitted in response to receipt of user input on a separate computing device. In embodiments, the indication is received by user input to skincare device 100 (for example, via user interface 113).

In embodiments, controller 101 is configured to determine at least one wavelength of light for use in scanning the one or more skin constituents. In embodiments, the determined at least one wavelength is associated with a frequency band outside of the visible spectrum. In embodiments, controller 101 is configured to determine the at least one wavelength of light by retrieving from a lookup table an entry corresponding to the indicated one or more skin constituents.

In embodiments, controller 101 is configured to control light source 109a (for example by generating corresponding control data 107a) to emit light at the determined at least one wavelength. In embodiments, light source 109a emits light having wavelengths within a predetermined a range of operation. In embodiments, controller 101 is configured to control light source 109a to suppress light emission at one or more wavelengths within that range of operation. Thus, controller 101 may be configured to control one or more light sources to selectively emit light (for example, according to wavelength).

In embodiments, light source 109a comprises a plurality of light emitting diodes. In such embodiments, it may be the at least one light emitting diode in the plurality is configured to emit light having a different wavelength to one or more other light emitting diodes in the plurality. In such cases, the wavelengths may be associated with different skin constituents. In embodiments, the controller 101 is configured to control the light source by controlling light emission by the plurality of light emitting diodes. In embodiments, controller 101 is configured to control light source 109a to cause one or more light emitting diodes in the plurality (for example, one or more light emitting diodes which do not correspond to the determined at least one wavelength) to cease to emit light. In embodiments, controller 101 is configured to control light source 109a to cause one or more light emitting diodes in the plurality (for example, one or more light emitting diodes which correspond to the determined at least one wavelength) which are not currently emitting light to start to emit light.

In embodiments, light source 109a comprises at least one variable wavelength light emitting diode. In such embodiments, it may be that controller 101 is configured to vary a wavelength of light emission by the at least one variable wavelength light emitting diode. It will be appreciated by the skilled person that light source 109a may comprise a plurality of light emitting diodes, one or more of which are variable wavelength light emitting diodes. Thus, controlling light source 109a may comprise both controlling light emission by the plurality of light emitting diodes and controlling a wavelength of light emission a variable wavelength light emitting diode.

As discussed above, in embodiments, skincare device 100 comprises sensor 103a. In such embodiments, sensor 103a may be configured to sense one or more characteristics of the user's skin. In embodiments, the one or more characteristics are associated with the presence of the identified one or more skin constituents. In embodiments, controller 101 is configured to control the sensor 103a to sense the one or more characteristics at the determined at least one wavelength.

FIG. 10 shows a flow chart illustrating the steps of a method 1000 of controlling a skincare device according to embodiments of the present disclosure.

A first step of method 1000, represented by item 1001, comprises controlling a light source to emit light onto a user's skin.

A second step of method 1000, represented by item 1003, comprises receiving an indication of one or more skin constituents for which the user's skin is to be scanned. In embodiments, the indication of the one or more constituents is associated with a skin feature. In embodiments, the device comprises a memory. In such embodiments, it may be that receiving the indication comprises retrieving from the memory a predetermined list of skin constituents to be scanned. In embodiments, the indication is received via a signal transmitted over a communications network. In such embodiments, it may be that the signal is transmitted in response to receipt of user input on a separate computing device. In embodiments, the indication is received by user input to the skincare device. In such embodiments, the user input may be provided by one or more of: pressing a button and providing a spoken command.

A third step of method 1000, represented by item 1005, comprises determining at least one wavelength of light for use in scanning the one or more skin constituents. In embodiments, the determined at least one wavelength is associated with a frequency band outside of the visible spectrum. In embodiments, determining the at least one wavelength of light comprises retrieving from a lookup table an entry corresponding to the indicated one or more skin constituents.

A fourth step of method 1000, represented by item 1007, comprises controlling the light source to emit light at the determined at least one wavelength. In embodiments, the light source emits light having wavelengths within a predetermined a range of operation. In such embodiments, it may be that controlling the light source comprises suppressing light emission at one or more wavelengths within the range of operation.

In embodiments, the light source comprises a plurality of light emitting diodes. In embodiments, it may be that at least one light emitting diode in the plurality is configured to emit light having a different wavelength to one or more other light emitting diodes in the plurality. In such embodiments, it may be that the different wavelengths are associated with different skin constituents. In embodiments, controlling the light source comprises controlling light emission by the plurality of light emitting diodes. In embodiments, controlling light emission by the plurality of light emitting diodes comprises causing at least one light emitting diode in the plurality to cease to emit light. In embodiments, controlling light emission by the plurality of light emitting diodes comprises causing light emitting diodes in the plurality which do not correspond to the determined at least one wavelength to cease to emit light. In embodiments, the light source comprises at least one wavelength-tuneable light emitting diode. In such embodiments, it may be that controlling the light source comprises controlling a wavelength of light emission by the wavelength-tuneable light emitting diode.

An optional fifth step of method 1000, represented by item 1009, comprises sensing one or more characteristics of the user's skin at the determined at least one wavelength. In embodiments, the one or more characteristics are associated with the presence of the one or more skin constituents.

It will be appreciated that method 1000 may be implemented by a computer program comprising a set of instructions, which, when executed by a computerised device, cause the computerised device to perform method 1000.

In embodiments, sensor 103a comprises a camera configured to capture an image of the user's skin. In embodiments, the camera comprises a visible light camera, configured to capture the image at one or more wavelengths within the visible spectrum. In embodiments, controller 101 is configured to identify in the captured image one or more portions of the user's skin for which an intensity of light is outside of a predetermined intensity range In embodiments, controller 101 is configured to control light source 109a to modify illumination of the identified one or more portions of the user's skin. In embodiments, controller 101 is configured to control the light source to modify illumination on the basis of the intensity of light. In embodiments, controller 101 is configured to, in response to the intensity of light being above an upper limit of the predetermined intensity range, control light source 109a to modify illumination to reduce the intensity of light emission onto the identified one or more portions. In embodiments, controller 101 is configured to, in response to the intensity of light being below a lower limit of the predetermined intensity range, control light source 109a to modify illumination to increase the intensity of light emission onto the identified one or more portions.

In embodiments, controller 101 is configured to identify in the captured image one or more further portions of the user's skin for which an intensity of light is outside of a predetermined intensity range. In such embodiments, it may be that controller 101 is configured to control light source 109a to modify illumination of the one or more further portions differently to the one or more portions. Where skincare device 100 comprises more than one light source, it may be that controller 101 is configured to modify illumination of the identified one or more portions and one or more further portions of the user's skin by controlling one or more (for example, all) of the multiple light sources 109. Thus, in embodiments, controller 101 is configured to control one or more light sources to selectively emit light (for example, according to which portion of the user's skin the light source is configured to emit light onto).

In embodiments, controller 101 is configured to identify in the captured image at least one wavelength of light at which an intensity is outside of a predetermined wavelength intensity range. In such embodiments, it may be that controller 101 is configured to control the light source to modify illumination of the user's skin at the identified at least one wavelength. In embodiments, the identified at least one wavelength is associated with the one or more portions of the user's skin. In embodiments, controller 101 is configured to control light source 109a to modify illumination at the identified at least one wavelength so as to illuminate the user's skin according to a specific colour rendering index.

In embodiments, the light source comprises a plurality of light emitting diodes. In embodiments, at least one light emitting diode in the plurality is configured to emit light onto a different part of the user's skin to one or more other light emitting diodes in the plurality. In such embodiments, it may be that controller 101 is configured to control light emission by the plurality of light emitting diodes to provide the modified illumination. In embodiments, controller 101 is configured to control light emission by the at least one light emitting diode differently to the one or more other light emitting diodes. In embodiments, controller 101 is configured to control each of the light emitting diodes in the plurality independently of one another. In embodiments, controller 101 is configured to control the light source to modify illumination by causing one or more of the light emitting diodes in the plurality (for example, light emitting diodes associated with a particular wavelength of light) to cease to emit light.

In embodiments, controller 101 is configured to receive an indication of a desired illumination of the user's skin. In some such embodiments, controller 101 is configured to control light source 109*a* to modify illumination on the basis of the received indication. In embodiments, the indication is received via a signal transmitted over a communications network (for example, via transceiver 117). In such embodiments, it may be that the signal is transmitted in response to receipt of user input on a separate computing device. In embodiments, the indication is received by user input to skincare device 100 (for example, via user interface 113).

In embodiments, the indication comprises an indication of a lighting condition (for example, daylight or artificial light). In such embodiments, it may be that controller 101 is configured to control light source 109*a* to modify light emission onto the user's skin to simulate the indicated lighting condition. In embodiments, the indication comprises an indication of a colour rendering index. In such embodiments, it may be that controller 101 is configured to control light source 109*a* to modify light emission onto the user's skin according to the indicated colour rendering index.

Figure 11:
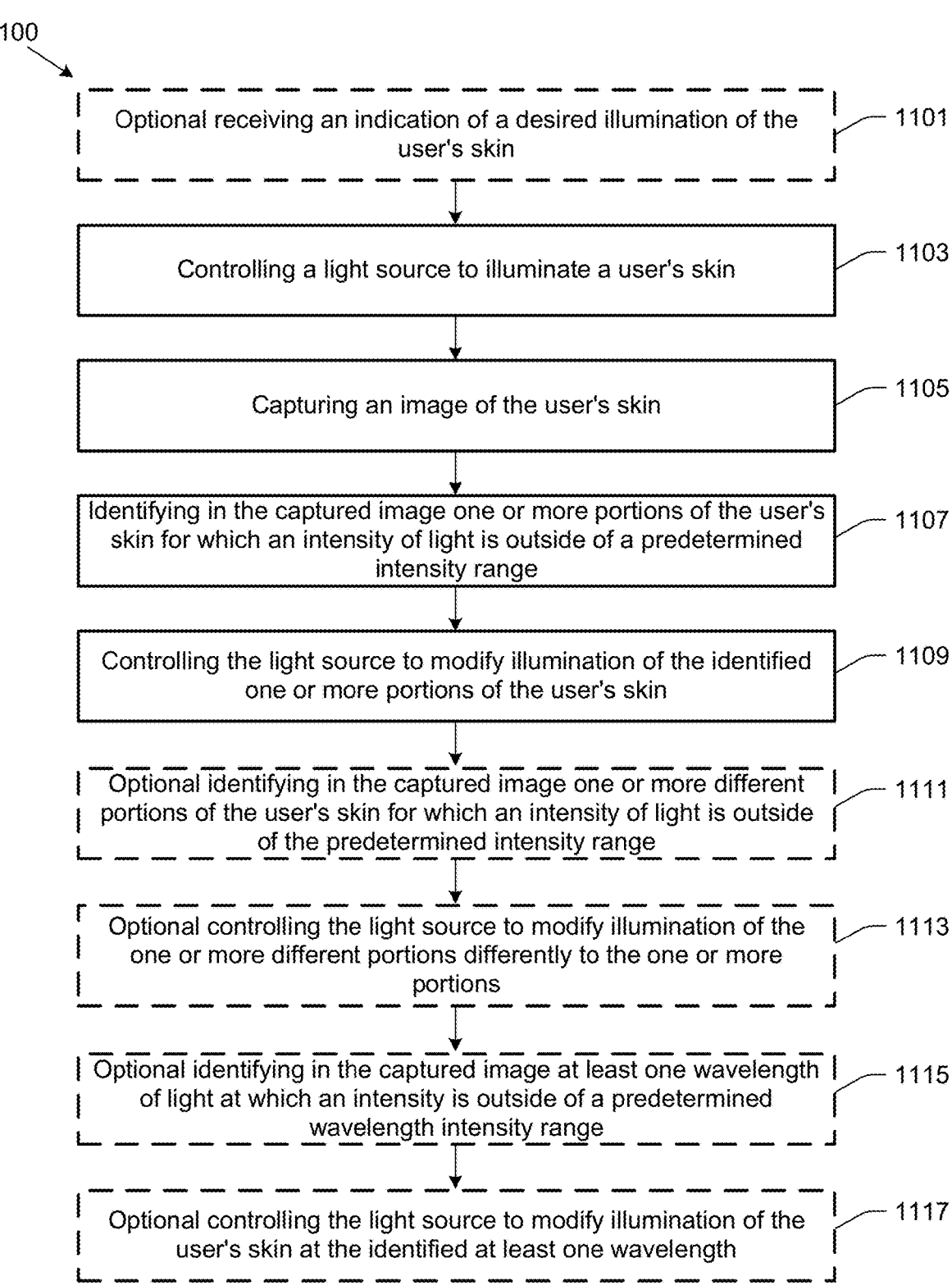

FIG. 11 shows a flow chart illustrating the steps of a method 1100 of controlling a skincare device according to embodiments of the present disclosure.

An optional first step of method 1100, represented by item 1101, comprises receiving an indication of a desired illumination of the user's skin. In embodiments, the indication is received via a signal transmitted over a communications network. In such embodiments, it may be that the signal is transmitted in response to receipt of user input on a separate computing device. In embodiments, the indication is received by user input to the device. In such embodiments, it may be that the user input comprises one or more of pressing a button and providing a spoken command.

A second step of method 1100, represented by item 1103, comprises controlling a light source to illuminate a user's skin. In embodiments, the controlling of the light source to modify illumination is dependent on the received indication.

A third step of method 1100, represented by item 1105, comprises capturing an image of the user's skin.

A fourth step of method 1100, represented by item 1107, comprises identifying in the captured image one or more portions of the user's skin for which an intensity of light is outside of a predetermined intensity range.

A fifth step of method 1100, represented by item 1109, comprises controlling the light source to modify illumination of the identified one or more portions of the user's skin. In embodiments, the controlling is performed on the basis of the intensity of light. In embodiments, the controlling comprises, in response to the intensity of light being above an upper limit of the predetermined intensity range, reducing the intensity of light emission onto the identified one or more portions. In embodiments, the controlling comprises, in response to the intensity of light being below a lower limit of the predetermined intensity range, increasing the intensity of light emission onto the identified one or more portions.

An optional sixth step of method 1100, represented by item 1111, comprises identifying in the captured image one or more different portions of the user's skin for which an intensity of light is outside of the predetermined intensity range.

An optional seventh step of method 1100, represented by item 1113, comprises controlling the light source to modify illumination of the one or more different portions differently to the one or more portions.

An optional eighth step of method 1100, represented by item 1115, comprises identifying in the captured image at least one wavelength of light at which an intensity is outside of a predetermined wavelength intensity range. In embodiments, the identified at least one wavelength is associated with the one or more portions of the user's skin.

An optional ninth step of method 1100, represented by item 1117, comprises controlling the light source to modify illumination of the user's skin at the identified at least one wavelength. In embodiments, controlling the light source to modify illumination at the identified at least one wavelength comprises controlling the light source to illuminate the user's skin according to a specific colour rendering index.

In embodiments, the light source comprises a plurality of light emitting diodes. In embodiments, it may be that at least one light emitting diode in the plurality is configured to emit light onto a different part of the user's skin to one or more other light emitting diodes in the plurality. In embodiments, the controlling comprises controlling light emission by the plurality of light emitting diodes to provide the modified illumination. In embodiments, the controlling comprises controlling light emission by at least one light emitting diode in the plurality differently to one or more other light emitting diodes in the plurality. In embodiments, the controlling comprises controlling each light emitting diode in the plurality independently of the other light emitting diodes in the plurality. In embodiments, controlling light emission by the plurality of light emitting diodes comprises causing at least one light emitting diode in the plurality to cease to emit light.

It will be appreciated that method 1100 may be implemented by a computer program comprising a set of instructions, which, when executed by a computerised device, cause the computerised device to perform method 1100.

In embodiments, sensor 103*a* comprises a visible light camera. In some such embodiments, sensor 103*a* is configured to capture a visible light image of a user's skin at one or more wavelengths within the visible spectrum. In embodiments, the visible light image is captured at a relatively high resolution (for example, greater than 10 megapixels). In embodiments, capturing the visible light image comprises capturing a plurality of visible light images of distinct parts of the user's skin. In such embodiments, it may be that controller 101 is configured to merge the captured plurality of visible light images to form the visible light image of the user's skin.

In embodiments, sensor 103*b* comprise a spectral sensor. In some such embodiments, sensor 103*b* is configured to capture a non-visible light image of the user's skin at one or more further wavelengths outside of the visible spectrum. In embodiments, the non-visible light image is captured at a relatively low resolution (for example, lower than 10 megapixels). In embodiments, capturing the non-visible light image comprises capturing a plurality of non-visible light images of distinct parts of the user's skin. In such embodiments, it may be that controller 101 is configured to merge the captured plurality of non-visible light images to form the non-visible light image of the user's skin.

In embodiments, controller 101 is configured to combine the visible light image and the non-visible light image to generate a composite image representative of the user's skin. In embodiments, controller 101 is configured to process the visible light image to identify one or more features within the visible light image. In embodiments, controller 101 is configured to process the non-visible light image to identify one or more corresponding features within the non-visible light image. In embodiments, controller 101 is configured to combine the visible light image and the non-visible light image on the basis of the features and the corresponding features (for example, by overlaying the visible light image and non-visible light image such that corresponding features within the visible light image and non-visible light image are aligned).

In embodiments, controller 101 is configured to transmit the generated composite image to a user interface (for example, user interface 113). In embodiments, the user interface is configured to display the composite image. In embodiments, the user interface is provided by a separate computing device. In such embodiments, controller 101 is configured to transmit (for example, by use of transceiver 117) the composite image to the separate computing device.

FIG. 12 shows a flow chart illustrating the steps of a method 1200 of controlling a skincare device according to embodiments of the present disclosure.

A first step of method 1200, represented by item 1201, comprises capturing a visible light image of a user's skin at one or more wavelengths within the visible spectrum. In embodiments, capturing the visible light image comprises capturing a plurality of visible light images of distinct parts of the user's skin. In such embodiments, it may be that capturing the visible light image comprises merging the captured plurality of visible light images to form the visible light image of the user's skin. In embodiments, the visible light image is captured at a relatively high resolution.

A second step of method 1200, represented by item 1203, comprises capturing a non-visible light image of the user's skin at one or more further wavelengths outside of the visible spectrum. In embodiments, capturing the non-visible light image comprises capturing a plurality of non-visible light images of distinct parts of the user's skin. In such embodiments, it may be that capturing the non-visible light image comprises merging the captured plurality of non-visible light images to form the non-visible light image of the user's skin. In embodiments, the non-visible light image is captured at a relatively low resolution.

An optional third step of method 1200, represented by item 1205, comprises processing the visible light image to identify one or more features within the visible light image.

An optional fourth step of method 1200, represented by item 1207, comprises processing the non-visible light image to identify one or more corresponding features within the non-visible light image.

A fifth step of method 1200, represented by item 1209, comprises combining the visible light image and the non-visible light image to generate a composite image representative of the user's skin. In embodiments comprising the third step 1205 and fourth step 1207, the combining is performed on the basis of the features and the corresponding features.

An optional sixth step of method 1200, represented by item 1211, comprises transmitting the generated composite image to a user interface configured to display the composite image. In embodiments, the device comprises the user interface. In embodiments, the user interface is provided by a separate computing device. In such embodiments, the transmitting comprises transmitting the composite image to the separate computing device.

It will be appreciated that method 1200 may be implemented by a computer program comprising a set of instructions, which, when executed by a computerised device, cause the computerised device to perform method 1200.

In embodiments, sensor 103*a* comprises a spectral sensor. In some such embodiments, sensor 103*a* is configured to capture a spectral image of a subject at one or more wavelengths outside of the visible spectrum. In embodiments, the one or more wavelengths are associated with the short wave infra-red spectrum. In embodiments, the one or more wavelengths comprise wavelengths between 1000 nm and 1700 nm. In embodiments, the one or more wavelengths comprise only wavelengths between 1000 nm and 1700 nm. As discussed above, in embodiments, the subject comprises a user's skin. However, in other embodiments, the subject may comprise a cosmetic bioplate.

In embodiments, controller 101 is configured to analyse the spectral image to determine a measure of cosmetic residue present on the subject. It will be understood by the skilled person that cosmetic residue refers to remnants of makeup or other cosmetic products, which remain on the subject after the subject has been cleaned. In embodiments, controller 101 is configured to determine the measure of cosmetic residue by identifying a portion of the spectral image having the lowest received signal strength at the one or more wavelengths. In such embodiments, it may be that controller 101 is configured to determine, for each of one or more further portions of the spectral image, a relative quantity of cosmetic residue by calculating a relative signal strength compared to the identified lowest signal strength.

In embodiments, controller 101 is configured to control sensor 103*a* to capture a calibration image during a calibration procedure initiated by the user. Such a calibration procedure may include steps of a user thoroughly cleaning the subject (such that the subject is in a "clean" state) and capturing a calibration image of the subject in the clean state for later use in identifying cosmetic residue on the subject. In such a procedure, a generic calibration subject may also be used in the place of the specific subject to be analysed. In embodiments, the calibration image is pre-stored in a memory (for example, memory 121) on the device. In embodiments, the analysis is performed in relation to a calibration image. In some such embodiments, controller 101 is configured to determine a measure of cosmetic residue present on the subject by comparing the captured spectral image with the calibration image. In embodiments, the comparing comprises identifying a difference in received signal strength between corresponding portions of the captured spectral image with the calibration image.

In embodiments, skincare device 100 may both have a calibration image pre-stored in memory and be configured to capture a calibration image during a calibration procedure initiated by the user. In such embodiments, it may be that controller 101 is configured to utilise the pre-stored calibration by default unless and until a calibration image is captured. In such cases, it may be that controller 101 is configured to, once a calibration image has been captured, utilise the captured calibration image instead of the pre-stored calibration image.

In embodiments, controller 101 is configured to control the skincare device to perform an action associated with the determined measure of cosmetic residue. In such embodiments, the action may comprise adjusting one or more operating settings of the skincare device. For example, the action may comprise adjusting one or more operating settings to cause the skincare device to perform one or more further analyses of the user's skin. In embodiments in which skincare device 100 comprises light source 109*a*, the action may comprise controlling one or more parameters of light emission by light source 109*a*.

In embodiments, the action comprises generating an alert. In such embodiments, it may be that the alert comprises a visible alert (for example, displayed on the display of user interface 113). In embodiments, the alert comprises an audible alert (for example, causing skincare device 100 to generate a sound). In embodiments, the alert comprises a tactile alert (for example, causing skincare device 100 to vibrate).

In embodiments, the action comprises providing an output to a user interface (for example, user interface 113). In embodiments, the user interface is provided by a separate computing device. In such embodiments, providing the output may comprise transmitting (for example, by transceiver 117) to the separate computing device a signal indicative of the output.

In embodiments in which the subject comprises a user's face, it may be that the output comprises an indication of a location on the user's face of the cosmetic residue. In some such embodiments, the action comprises causing the user interface to display an image of a face highlighting the indicated location. In embodiments, the image comprises an image of the user's face. In alternative embodiments, the image comprises a generic image of a face.

In embodiments in which the subject comprises a cosmetic bioplate, it may be that the output comprises an indication of a location on the cosmetic bioplate of the cosmetic residue. In some such embodiments, the action comprises causing the user interface to display an image of the cosmetic bioplate highlighting the indicated location.

FIG. 13 shows a flow chart illustrating the steps of a method 1300 of controlling a skincare device according to embodiments of the present disclosure.

An optional first step of method 1300, represented by item 1301, comprises capturing a calibration image during a calibration procedure initiated by the user.

A second step of method 1300, represented by item 1303, comprises capturing a spectral image of a subject at one or more wavelengths outside of the visible spectrum. In embodiments, the subject comprises one of: a user's skin and a cosmetic bioplate.

A third step of method 1300, represented by item 1305, comprises analysing the spectral image to determine a measure of cosmetic residue present on the subject. In embodiments, the determining comprises identifying a portion of the spectral image having the lowest received signal strength at the one or more wavelengths. In embodiments, the determining comprises determining, for each of one or more further portions of the spectral image, a relative quantity of cosmetic residue by calculating a relative signal strength compared to the identified minimum signal strength. In embodiments comprising the first step 1301, it may be that the analysing is performed in relation to the calibration image. Alternatively, the calibration image may be pre-stored in a memory on the skincare device.

A fourth step of method 1300, represented by item 1307, comprises controlling the skincare device to perform an action associated with the determined measure of cosmetic residue. In embodiments, the action comprises adjusting one or more operating settings of the skincare device. In embodiments, the action comprises generating an alert. In such embodiments, it may be that the alert comprises one or more of: a visible alert, an audible alert, and a tactile alert. In embodiments, the device comprises a light source configured to emit light onto the user's skin. In some such embodiments, the action comprises controlling one or more parameters of light emission by the light source. In embodiments, the action comprises providing an output to a user interface. In embodiments in which the subject comprises a user's face, it may be that the output comprises an indication of a location on the user's face of the cosmetic residue. In some such embodiments, the action comprises causing the user interface to display an image of a face highlighting the indicated location. In embodiments, the image comprises an image of the user's face. In alternative embodiments, the image comprises a generic image of a user's face. In embodiments in which the subject comprises a cosmetic bioplate, it may be that the output comprises an indication of a location on the cosmetic bioplate of the cosmetic residue. In some such embodiments, the action comprises causing the user interface to display an image of the cosmetic bioplate highlighting the indicated location. In embodiments, the skincare device comprises the user interface. In alternative embodiments, the user interface is provided by a separate computing device. In such embodiments, it may be that providing the output comprises transmitting to the separate computing device a signal indicative of the output.

It will be appreciated that method 1300 may be implemented by a computer program comprising a set of instructions, which, when executed by a computerised device, cause the computerised device to perform method 1300.

In embodiments, sensor 103*a* is configured to sense, in a first frequency band, one or more characteristics of a user's skin. Thus, in such embodiments, sensor 103*a* can be said to be of a first type. In embodiments, the first frequency band comprises one or both of visible light and near infra-red wavelengths. In embodiments, the first frequency band comprises only visible light and/or near infra-red wavelengths. In embodiments, the first frequency band comprises wavelengths between 400 nm and 1000 nm. In embodiments, the first frequency band comprises only wavelengths between 400 nm and 1000 nm.

In embodiments, controller 101 comprises a classifier. In embodiments the classifier has been trained using a sensor of the first type, configured to sense, in the first frequency band, one or more characteristics of the skin of a corpus of training users. In such embodiments, it may be that training of the classifier was also performed using a sensor of a second type, configured to sense, in a different second frequency band, a moisture content of the skin of the corpus of training users. In embodiments, the classifier comprises a machine learning agent. In embodiments, the classifier is trained to determine the moisture content on the basis of the sensed one or more characteristics. In such embodiments, it may be that the training comprises treating the output of the sensor of the second type as a ground truth. In embodiments, the second frequency band comprises wavelengths outside of the visible and near infra-red spectrum. In embodiments, the second frequency band corresponds to short wave infra-red radiation. In embodiments, the second frequency band comprises wavelengths between 1000 nm and 1700 nm. In embodiments, the first frequency band comprises only wavelengths between 1000 nm and 1700 nm. In embodiments, controller 101 is configured to provide the sensed one or more characteristics of the user's skin to the trained classifier. In embodiments, controller 101 is configured to operate the trained classifier to determine a moisture content of the user's skin.

In embodiments, the device does not comprise a sensor of the second type.

In embodiments, controller 101 is configured to control the skincare device to perform an action associated with the determined moisture content. In embodiments, the action comprises adjusting one or more operating settings of the skincare device. For example, the action may comprise adjusting one or more operating settings to cause the skincare device to perform one or more further analyses of the user's skin. In embodiments in which skincare device 100 comprises light source 109a, the action may comprise controlling one or more parameters of light emission by light source 109a.

In embodiments, the action comprises generating an alert. In such embodiments, it may be that the alert comprises a visible alert (for example, displayed on the display of user interface 113). In embodiments, the alert comprises an audible alert (for example, causing skincare device 100 to generate a sound). In embodiments, the alert comprises a tactile alert (for example, causing skincare device 100 to vibrate).

In embodiments, the action comprises providing an output to a user interface (for example, user interface 113). In embodiments, the user interface is provided by a separate computing device. In such embodiments, providing the output may comprise transmitting (for example, by transceiver 117) to the separate computing device a signal indicative of the output.

Figure 14:
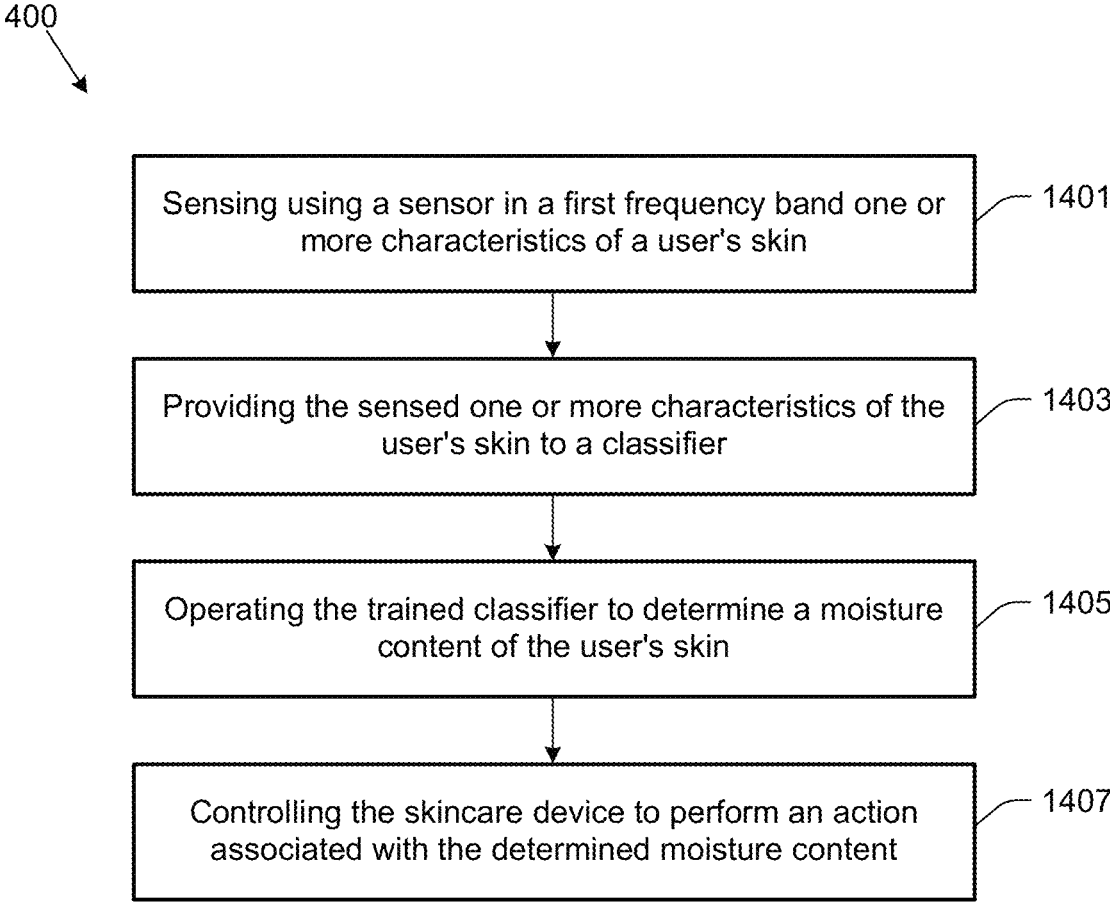

FIG. 14 shows a flow chart illustrating the steps of a method 1400 of controlling a skincare device according to embodiments of the present disclosure.

A first step of method 1400, represented by item 1401, comprises sensing, using a sensor of a first type, in a first frequency band, one or more characteristics of a user's skin. In embodiments, the first frequency band comprises only one or both of visible light and near infra-red wavelengths. In embodiments, the first frequency band comprises wavelengths between 400 nm and 1000 nm. In embodiments, the first frequency band comprises only wavelengths between 400 nm and 1000 nm.

A second step of method 1400, represented by item 1403, comprises providing the sensed one or more characteristics of the user's skin to a classifier. In embodiments, the classifier has been trained using a sensor of the first type, configured to sense, in the first frequency band, one or more characteristics of the skin of a corpus of training users, and a sensor of a second type, configured to sense, in a different second frequency band, a moisture content of the skin of the corpus of training users. In embodiments, the classifier comprises a machine learning agent. In embodiments, the classifier is trained to determine the moisture content on the basis of the sensed one or more characteristics. In embodiments, the second frequency band comprises wavelengths outside of the visible and near infra-red spectrum. In embodiments, the second frequency band comprises wavelengths between 1000 nm and 1700 nm. In embodiments, the first frequency band comprises only wavelengths between 1000 nm and 1700 nm.

A third step of method 1400, represented by item 1405, comprises operating the trained classifier to determine a moisture content of the user's skin.

A fourth step of method 1400, represented by item 1407, comprises controlling the skincare device to perform an action associated with the determined moisture content. In embodiments, the action comprises adjusting one or more operating settings of the skincare device. In embodiments, the action comprises generating an alert, wherein the alert comprises one or more of: a visible alert, an audible alert, and a tactile alert. In embodiments, the device comprises a light source configured to emit light onto the user's skin. In such embodiments, it may be that the action comprises controlling one or more parameters of light emission by the light source. In embodiments, the action comprises providing an output to a user interface. In embodiments, the skincare device comprises the user interface. In embodiments, the user interface is provided by a separate computing device. In such embodiments, it may be that providing the output comprises transmitting to the separate computing device a signal indicative of the output.

It will be appreciated that method 1400 may be implemented by a computer program comprising a set of instructions, which, when executed by a computerised device, cause the computerised device to perform method 1400.

In embodiments, the skincare device 100 is configured to adjust a skincare regimen of a user. A skincare regimen will be understood to be a program/schedule for application of one or more light therapy regimes or skincare formulations to the skin.

In such embodiments, the skincare device 100 includes a spectral sensor 103a configured to generate spectral data 105a associated with the skin of the user, by sensing light at frequency bands both inside and outside of the visible spectrum reflected from, or emitted by, the skin of the user. The skincare device 100 may also include a further spectral sensor 103b configured to generate spectral data 105b associated with the skin of the user.

The controller 101 is configured to establish a predetermined skincare regimen of the user, wherein the predetermined skincare regimen comprises a plurality of variable elements. The predetermined skincare regimen is established via user input for example through a user interface 113. In other embodiments, the predetermined skincare regimen is established via download from a database 123 (for example a remote database 'in the cloud'). The variable elements comprise elements of a skincare formulation regime for example, types of skincare formulations, amounts/concentrations of active and/or base substances in the formulations, methods of application of the formulations including for example regions of the skin, time intervals between applications and/or number of applications. In embodiments, the variable elements comprise types of treatment device. A treatment device will be understood to be a device delivering (or aiding delivery of) a skincare product or skincare regimen, for example a microneedle or an ultrasound device. In other embodiments, the variable elements comprise elements of a light therapy regime for example light intensities, durations of exposure, time intervals between exposures, number of exposures and/or regions of the skin to be exposed.

The controller 101 is further configured to, after a first pre-set time period, cause the one or more spectral sensors 103a, 103b to generate spectral data 105a, 105b, by sensing light at a frequency band both inside and outside of the visible spectrum reflected from, or emitted by, the skin of the user. In embodiments, the first pre-set time period is part of the predetermined skincare regimen. During the first pre-set time period, the user follows the predetermined skincare regimen. In embodiments, the first pre-set time period is a number of days, for example 1 day, 2 days, 3 days or more than 3 days. The spectral data 105a, 105b, generated after the first time period is therefore indicative of the user's response to the predetermined skincare regimen.

In embodiments, the light is sensed using one or more spectral sensors. In embodiments the light is sensed at frequency bands both inside and outside of the visible spectrum.

The controller 101 is further configured to process the spectral data 105a, 105b, to determine the user's physiological response to the predetermined skincare regimen during the first pre-set time period. In embodiments, the physiological response includes a measure of skin state for example moisture level and/or elasticity of the user's skin.

The controller 101 is further configured to vary one or more of the variable elements to provide a varied skincare regimen.

The controller 101 is configured to, after a second pre-set time period, cause the one or more spectral sensors 103*a*, 103*b*, to generate further spectral data 105*a*, 105*b*, by sensing light at frequency bands both inside and outside of the visible spectrum reflected from, or emitted by, the skin of the user. In embodiments, the second pre-set time period is part of the predetermined skincare regimen. During the second pre-set time period, the user follows the predetermined skincare regimen. In embodiments, the second pre-set time period is a number of days, for example 1 day, 2 days, 3 days or more than 3 days. The spectral data 105*a*, 105*b*, generated after the second time period is therefore indicative of the user's response to the varied skincare regimen.

The controller 101 is further configured to process the further spectral data 105*a*, 105*b*, from the second scan to determine the user's physiological response to the varied skincare regimen during the second pre-set time period.

The controller 101 is further configured to determine an updated skincare regimen based on a comparison of the determined physiological responses to the predetermined skincare regimen and the varied skincare regimen. In embodiments, the physiological responses are compared, and if the skin state has improved overall, then the updated skincare regimen is set to match the varied skincare regimen. If the skin state has improved in only some aspects, the updated skincare regimen is set to partially match the varied skincare regimen, for example incorporating the same skincare formulation but applied at different intervals. If the skin state has not improved, then the updated skincare regimen is set to match the predetermined skincare regimen.

The controller 101 is further configured to control the skincare device 100 to perform one or more actions associated with the updated skincare regimen. In embodiments, the one or more actions comprise adjusting one or more operating settings of the skincare device. In embodiments, the one or more actions comprise generating an alert, wherein the alert comprises one or more of: a visible alert, an audible alert, and a tactile alert. In embodiments, the one or more actions comprise providing an output associated with the predetermined, varied, updated and/or optimized skincare regimens to a user interface. The skincare device 100 may comprise the user interface. In alternative embodiments, the user interface is provided by a separate computing device and providing the output comprises transmitting a signal to the separate computing device. In embodiments, the one or more actions comprise storing in a database 123 in the cloud, an output associated with the predetermined, varied and/or updated skincare regimens.

The controller 101 is further configured to iteratively repeat the step of varying one or more of the variable elements at least once through to the step of determining an updated skincare regimen, wherein in each iteration a different variation is made (i.e. a different variable element is varied, or the same variable element is varied in a different way).

The controller 101 is further configured to determine an optimised skincare regimen for the user, by comparing the physiological responses determined in respective iterations, wherein the optimized skincare regimen provides the maximum expected positive physiological response of the user.

In embodiments, the controller 101 is configured to retrieve from a database 123, physiological response data associated with one or more additional users. In such embodiments, the controller 101 is configured to determine an optimised skincare regimen for the user, by comparing the physiological responses of the user with the physiological response data associated with the one or more additional users. In such embodiments, the database 123 is in the cloud.

In embodiments, the controller 101 is configured to determine the optimised skincare regimen for the user by maximising an information gain.

In embodiments, the controller 101 is configured to determine a correlation between skincare regimen and physiological response.

In embodiments, the device comprises a light source configured to emit light onto the user's skin, and the one or more actions comprise controlling one or more parameters of light emission by the light source.

In embodiments, the pre-set time periods are set by the user. The first pre-set time period is, for example, 4, 6, 12, 24, or 48 hours, or shorter/longer. In embodiments, the second pre-set time period is 4, 6, 12, 24, or 48 hours or shorter/longer.

In embodiments, the spectral data 105*a*, 105*b*, is hyperspectral data.

In embodiments, the variable elements comprise any of: one or more light therapy intensities or durations; one or more skincare formulations; one or more time intervals; one or more regions of the user's skin; and one or more concentrations or amounts of active substances in the skincare formulations.

FIG. 15 shows a flow chart illustrating the steps of a method 1500 of controlling a skincare device to adjust a skincare regimen of a user, according to embodiments of the present disclosure.

A first step of method 1500, represented by item 1501, comprises establishing a predetermined skincare regimen, wherein the predetermined skincare regimen comprises a plurality of variable elements.

A second step of method 1500, represented by item 1503, comprises after a first pre-set time period, sensing light at a frequency band inside and outside of the visible spectrum reflected from, or emitted by, the skin of the user to generate spectral data.

A third step of method 1500, represented by item 1505, comprises processing the spectral data from the first scan to determine the user's physiological response to the predetermined skincare regimen during the first pre-set time period.

A fourth step of method 1500, represented by item 1507, comprises varying one or more of the variable elements to provide a varied skincare regimen.

A fifth step of method 1500, represented by item 1509, comprises after a second pre-set time period, sensing light at a frequency band inside and outside of the visible spectrum reflected from, or emitted by, the skin of the user to generate further spectral data.

A sixth step of method 1500, represented by item 1511, comprises processing the further spectral data from the second scan to determine the user's physiological response to the varied skincare regimen during the second pre-set time period.

A seventh step of method 1500, represented by item 1513, comprises determining an updated skincare regimen by comparing the determined physiological responses to the predetermined skincare regimen and the varied skincare regimen.

An eighth step of method 1500, represented by item 1513, comprises controlling the skincare device to perform one or more actions associated with the updated skincare regimen.

It will be appreciated that method 1500 may be implemented by a computer program comprising a set of instructions, which, when executed by a computerised device, causes the computerised device to perform method 1500.

In embodiments, the controller 101 is configured to: receive spectral data 105a, 105b, associated with the skin of a user; process the spectral data 105a, 105b, using a trained classification algorithm to identify a skin type cluster to which the user's skin corresponds; retrieve, from a skincare regimen database, skincare regimen data associated with the identified skin type cluster; and control the skincare device 100 to perform one or more actions associated with the retrieved skincare regimen data. It will be understood that sensor data comprises spectral data. In embodiments, the skincare regimen database is part of database 123. In embodiments, the skincare regimen database is a separate database in the cloud.

In embodiments, the skincare regimen data associated with the identified skin type cluster comprises, for each of a plurality of individuals in the skin type cluster, one or more of: skincare formulation data; application time interval data; application method data; skin region data; and spectral data associated with the skin of the individual. Skincare formulation data will be understood to be data relating to one or more skincare formulations. Application method data will be understood to be data relating to methods of applying one or more skincare formulations to the skin, for example the orders in which skincare formulations are applied, or the techniques for applying them to the skin. Application time interval data will be understood to be data relating to the time intervals between applications of skincare formulations to the skin. Skin region data will be understood to be data relating to regions/areas of the skin to which the skincare formulations are applied. In embodiments, the spectral data associated with the skin of the individual is associated with a particular skincare regimen and reflects the skin condition of the individual after one or more time periods.

In embodiments, processing the spectral data 105a, 105b, associated with the skin of a user comprises deriving values for one or more skin states. In embodiments, the skin states comprise one or more of: skin age; skin moisture level; skin oil level; skin elasticity, skin fat content, skin protein content, skin oxygenation levels, skin topography, skin roughness, skin colour, skin tone and skin gloss.

In embodiments, processing the spectral data 105a, 105b, associated with the skin of a user comprises weighting the derived values for the one or more skin states on the basis of predicted significance levels. In certain embodiments, the weightings are from 0 to 1 (alternative weightings may be used).

In embodiments, the controller 101 is further configured to determine one or more skincare regimen recommendations specific to the user from the retrieved skincare regimen data; and the one or more actions are associated with the skincare regimen recommendations.

In embodiments, the one or more skincare regimen recommendations comprise at least one of: a skincare formulation; an application time interval; an application method; and a skin region.

In embodiments, the one or more actions comprise providing an output to a user interface, wherein the controller 101 is further configured to cause the user interface to display the one or more skincare regimen recommendations. In embodiments, the skincare device 100 comprises the user interface. In alternative embodiments, the user interface is provided by a separate computing device; and providing the output comprises transmitting a signal to the separate computing device.

In embodiments, the one or more actions comprise adjusting one or more operating settings of the skincare device 100. In embodiments, the one or more actions comprise generating an alert, wherein the alert comprises one or more of: a visible alert, an audible alert, and a tactile alert.

In embodiments, the skincare device 100 comprises a light source configured to emit light onto the user's skin; and the one or more actions comprise controlling one or more parameters of light emission by the light source.

In embodiments, the skincare device 100 further comprises one or more spectral sensors 103a, 103b configured to generate the spectral data 105a, 105b, associated with the skin of a user by sensing light at frequency bands both inside and outside of the visible spectrum reflected from, or emitted by, the skin of the user.

In embodiments, the spectral data associated with the skin of the user comprises hyperspectral data.

In embodiments, the spectral data 105a, 105b associated with the skin of the user is received from a remote sensing device configured to sense light at frequency bands both inside and outside of the visible spectrum reflected from, or emitted by, the skin of the user.

FIG. 16a shows a flow chart illustrating the steps of a method 1600 of controlling a skincare device 100 according to embodiments of the present disclosure.

A first step of method 1600, represented by item 1601, comprises receiving at a controller 101, spectral data 105a, 105b, associated with a user's skin.

A second step of method 1600, represented by item 1603, comprises processing the spectral data 105a, 105b, associated with the user's skin using a trained classification algorithm to identify a skin type cluster to which the user's skin corresponds.

A third step of method 1600, represented by item 1605, comprises retrieving from a skincare regimen database, skincare regimen data associated with the identified skin type cluster.

A fourth step of method 1600, represented by item 1607, comprises controlling the skincare device 100 to perform one or more actions associated with the retrieved skincare regimen data.

It will be appreciated that method 1600 may be implemented by a computer program comprising a set of instructions, which, when executed by a computerised device, causes the computerised device to perform method 1600.

FIG. 16b shows a flow chart illustrating the steps of a method 1602 of training a classification algorithm for use in controlling a skincare device 100 to identify a skin type cluster to which a user's skin corresponds, according to embodiments of the present disclosure.

A first step of method 1602, represented by item 1609, comprises for each user of a corpus of training users, using one or more spectral sensors 103a, 103b, to generate spectral data associated with each training user's skin, by sensing light at frequency bands both inside and outside of the visible spectrum reflected from, or emitted by, each training user's skin.

A second step of method 1602, represented by item 1611, comprises training the classification algorithm by monitoring clustering of the corpus of training users into skin type clusters based on the stored spectral data and a plurality of skin states.

FIG. 16c shows a flow chart illustrating the steps of a method 1604 of constructing a skincare regimen database using a classification algorithm, according to embodiments of the present disclosure.

A first step of method 1604, represented by item 1613, comprises, for each of a plurality of users with a plurality of associated skin regimens, using one or more spectral sensors 103a, 103b, to generate spectral data associated with each user's skin, by sensing light at frequency bands both inside and outside of the visible spectrum reflected from, or emitted by, each user's skin.

A second step of method 1604, represented by item 1615, comprises processing the spectral data for each user using a trained classification algorithm to identify a skin type cluster to which the user's skin corresponds.

A third step of method 1604, represented by item 1617, comprises storing the spectral data, data associated with the skin regimens, and data associated with the identified skin type clusters in the skin regimen database.

A fourth optional step of method 1604, represented by item 1619, comprises after a predetermined time interval, repeating steps one to two of the method for the same plurality of users.

A fifth optional step of method 1604, represented by item 1621, comprises updating the stored spectral data, data associated with the skin regimens, and data associated with the identified skin type clusters in the skin regimen database.

In embodiments, the skincare device 100 is configured to analyse the skin of a user. The controller 101 is configured to: receive spectral data 105a, 105b, associated with the skin of the user; process the spectral data 105a, 105b, using a trained classifier to identify the presence of one or more spectral profiles, each spectral profile being associated with a respective metabolic constituent and comprising one or more characteristic wavelengths; and control the skincare device 100 to perform one or more actions associated with the one or more identified spectral profiles. A spectral profile will be understood to be a pattern in the spectral data 105a, 105b.

In embodiments, the controller 101 is further configured to determine, from each identified spectral profile, an amount of the respective metabolic constituent in the skin of the user.

In embodiments, the determined amounts of metabolic constituents in the skin of the user are relative amounts, representing the proportionate composition of the user's skin, the relative amounts determined by comparing the one or more spectral profiles at their respective characteristic wavelengths.

In embodiments, the metabolic constituents comprise one or more of water, lipid, protein, haemoglobin, sebum and melanin.

The controller 101 is further configured to adjust the one or more spectral profiles on the basis of a determined amount of melanin in the skin of the user.

In embodiments, the controller 101 is further configured to transmit information to a user interface 113, and the one or more actions comprise transmitting to the user interface 113 information relating to the one or more spectral profiles and/or respective metabolic constituents.

In embodiments, the skincare device 100 further comprises the user interface 113, and the one or more actions comprise displaying on the user interface 113 the information relating to the one or more spectral profiles and/or respective metabolic constituents.

In embodiments, the controller 101 is further configured to transmit information to a remote user interface on a connected device.

In embodiments, the classifier comprises a regression algorithm.

In embodiments, the spectral data 105a, 105b, comprises hyperspectral data.

In embodiments, the device 100 further comprises one or more spectral sensors 103a, 103b, configured to generate the spectral data 105a, 105b, by sensing light at frequency bands both inside and outside of the visible spectrum reflected from, or emitted by, the skin of the user. In other embodiments, the controller 101 is configured to receive spectral data 105a, 105b, generated by, and transmitted from, a remote sensing device configured to sense light at frequency bands both inside and outside of the visible spectrum reflected from, or emitted by, the skin of the user.

In embodiments, the one or more actions comprise one or more of determining skin age, skin moisture level, skin oil level, skin elasticity, skin fat content, skin protein content, skin oxygenation levels, skin topography, skin roughness, skin colour, skin tone and skin gloss based on the identified spectral profiles, to provide an indication of skin type and/or health. Skin moisture level may alternatively be known as skin hydration.

FIG. 17a shows a flow chart illustrating the steps of a computer-implemented method 1700 of analysing the skin of a user, according to embodiments of the present disclosure.

A first step of method 1700, represented by item 1701, comprises receiving, at a controller 101, spectral data 105a, 105b, associated with the skin of the user.

A second step of method 1700, represented by item 1703, comprises processing the spectral data 105a, 105b, using a trained classifier to identify the presence of one or more spectral profiles, each spectral profile associated with a respective metabolic constituent and comprising one or more characteristic wavelengths.

A third step of method 1700, represented by item 1705, comprises controlling the skincare device to perform one or more actions associated with the one or more identified spectral profiles.

A fourth optional step of method 1700, represented by item 1707, comprises generating locally within the skincare device 100, the spectral data 105a, 105b, by sensing light at frequency bands both inside and outside of the visible spectrum reflected from, or emitted by, the skin of the user, and providing the spectral data 105a, 105b, to the controller 101.

An alternative fourth optional step of method 1700, represented by item 1709, comprises generating at a remote device, the spectral data 105a, 105b, by sensing light at a frequency band inside and outside of the visible spectrum reflected from, or emitted by, the skin of the user, and transmitting the spectral data 105a, 105b, to the controller 101.

It will be appreciated that method 1700 may be implemented by a computer program comprising a set of instructions, which, when executed by a computerised device, causes the computerised device to perform method 1700.

FIG. 17b shows a flow chart illustrating the steps of a computer-implemented method 1702 of training a classifier for use in analysing the skin of a user, according to embodiments of the present disclosure.

A first step of method 1702, represented by item 1711, comprises training the classifier by, for a first metabolic constituent: inputting spectral data associated with the first metabolic constituent, the spectral data obtained from a corpus of training users by sensing light at frequency bands both inside and outside of the visible spectrum reflected from, or emitted by, the skin of each of the training users; and monitoring identification by the classifier, for each of the training users, of the presence of a spectral profile associated with the first metabolic constituent. In embodiments, the step of monitoring identification by the classifier of the presence of the spectral profile associated with the first metabolic constituent comprises monitoring the identification of the presence of one or more characteristic wavelengths of the spectral profile.

A second step of method 1702, represented by item 1713, comprises repeating the training steps for one or more further metabolic constituents.

In embodiments, it is desirable to know the different components which make up a user's skin. In embodiments, devices and methods are proposed which provide an iterative modelling approach to determining skin composition. In embodiments, the skincare device 100 is configured to determine a user's skin composition by modelling skin components based on light reflectance/absorption from the user's skin. It is assumed that the total light absorption by the user's skin is the sum of the light absorption from at least one metabolic constituent component of the user's skin and at least one noise term.

In embodiments, an N component model is fit to a received light signal comprising spectral data associated with the skin of a user (i.e. obtained by spectral imaging of the user's skin).

The controller 101 is configured to: (step one) receive spectral data associated with the skin of a user; (step two) determine a skin composition model comprising a number of components $N=N_0$, the components comprising at least one noise component and at least one metabolic constituent component; (step three) apply an information criterion to the model to spectrally un-mix and de-noise the spectral data, to determine a skin composition model suitability rating, wherein the information criterion comprises a term representing closeness of fit of the model to the received sensor data, and a penalty term associated with model complexity; (step four) add a further metabolic constituent component to the model, such that $N=N+1$, and iteratively repeating steps three and four at least once; (step five) select a preferred model by comparing model suitability ratings of respective iterations; and (step six) cause performing of one or more actions associated with the preferred skin composition model. Spectral un-mixing will be understood to be separation of spectral data into a series of spectral profiles. Each spectral profile is representative of a metabolic constituent of the skin. Spectral data tends to include noise, and de-noising will be understood to be the removal of the noise from the spectral data.

In embodiments, the device 100 further comprises one or more spectral sensors 103a, 103b, configured to generate the spectral data 105a, 105b, by sensing light at frequency bands both inside and outside of the visible spectrum reflected from, or emitted by, the skin of the user, wherein the controller 101 is configured to receive the spectral data 105a, 105b, from the one or more spectral sensors 103a, 103b. Alternatively, or in addition, in embodiments, the controller 101 is configured to receive the spectral data 105a, 105b from a remote sensing device configured to sense light at frequency bands both inside and outside of the visible spectrum reflected from, or emitted by, the skin of the user.

FIG. 18 shows a flow chart illustrating the steps of a computer-implemented method 1800 of determining a user's skin composition, according to embodiments of the present disclosure.

A first step of method 1800, represented by item 1801, comprises receiving spectral data associated with the skin of a user.

A second step of method 1800, represented by item 1803, comprises determining a skin composition model comprising a number of components $N=N_0$, the components comprising at least one noise component and at least one metabolic constituent component.

A third step of method 1800, represented by item 1805, comprises applying an information criterion to the model to spectrally un-mix and de-noise the spectral data, to determine a skin composition model suitability rating, wherein the information criterion comprises a term representing closeness of fit of the model to the received sensor data, and a penalty term associated with model complexity.

A fourth step of method 1800, represented by item 1807, comprises adding a further metabolic constituent component to the model, such that $N=N+1$, and iteratively repeating the third and fourth steps at least once.

A fifth step of method 1800, represented by item 1809, comprises selecting a preferred model by comparing model suitability ratings of respective iterations.

A sixth step of method 1800, represented by item 1811, comprises performing one or more actions associated with the preferred model, or controlling a skincare device to perform such one or more actions.

In embodiments, the step of determining a number of components $N=N_0$ comprises selecting from a list of metabolic constituent components based on predicted metabolic constituent abundances.

In embodiments, the list of metabolic constituent components comprises water, lipid, protein, haemoglobin, collagen, elastin, sebum and melanin.

In embodiments, $N_0=2$ including the metabolic constituent component of water, and a noise component.

In embodiments, the noise component comprises a Gaussian white noise component.

In embodiments, in subsequent iterations, the other metabolic constituent components are added successively one by one (not necessarily in that order)

In embodiments, the penalty term is proportional to N.

In embodiments, selecting an iteration by comparing model suitability ratings of respective iterations comprises selecting an iteration with an optimum model suitability rating.

In embodiments, selecting an iteration with an optimum model suitability rating comprises searching for a global minimum in respect of model suitability rating versus N.

In embodiments, the information criterion is applied to the model to simultaneously spectrally un-mix and de-noise the spectral data.

In embodiments, the information criterion comprises a Bayesian criterion or an Akaike criterion.

In embodiments, the spectral data comprises hyperspectral data.

A further, optional, step of method 1800 (not shown in FIG. 18), comprises locally generating the spectral data 105a, 105b, by sensing light at frequency bands both inside and outside of the visible spectrum reflected from, or emitted by, the skin of the user; and transmitting the spectral data 105a, 105b, to the controller 101, wherein the controller is configured to undertake steps one to six.

Alternatively, the further, optional, step of method 1800 comprises remotely generating the spectral data by sensing light at frequency bands both inside and outside of the visible spectrum reflected from, or emitted by, the skin of the user; and transmitting the spectral data to the controller 101, wherein the controller is configured to undertake steps one to six.

In embodiments, the one or more actions comprise outputting data associated with the preferred model.

In embodiments, the one or more actions comprise generating an alert, wherein the alert comprises one or more of: a visible alert, an audible alert, and a tactile alert.

In embodiments, a skincare device is configured to perform the method. In other embodiments, the method is performed on a separate computing device.

It will be appreciated that method 1800 may be implemented by a computer program comprising a set of instructions, which, when executed by a computerised device, causes the computerised device to perform method 1800.

In embodiments, the skincare device 100 is configured to dispense a skincare product. The device 100 comprises a plurality of cartridges (not shown in FIG. 1) configured to hold a plurality of active substances and one or more base substances.

The controller 101 is configured to: receive spectral data 105a, 105b, associated with the skin of a user; process the spectral data 105a, 105b, to identify the presence of one or more skin constituents of the skin of the user; and on the basis of the identified one or more skin constituents, determine a skincare product formulation specific to the user comprising at least one active substance and at least one base substance.

The device 100 further comprises a dispenser (not shown in FIG. 1) configured to receive active and base substances from the plurality of cartridges and mix and dispense a skincare product according to the determined skincare product formulation specific to the user.

In embodiments, the one or more skin constituents comprises (i) one or more metabolic constituents of the user's skin selected from a list comprising water, lipid, protein, melanin, haemoglobin, collagen, elastin and/or sebum, and/or (ii) one or more skin states of the user's skin selected from a list comprising skin age, skin moisture level, skin oil level, skin elasticity, skin fat content, skin protein content, skin oxygenation levels, skin topography, skin roughness, skin colour, skin tone and skin gloss.

In embodiments, the controller 101 is further configured to determine a first optimal concentration specific to the user of at least one of the active substances in at least one of the base substances.

In embodiments, the controller 101 is further configured to determine a second optimal concentration specific to the user of at least one of the active substances in at least one of the base substances.

In embodiments, the controller 101 is further configured to determine an optimal quantity of the first optimal concentration relative to the second further optimal concentration, in the skincare product formulation specific to the user.

In embodiments, the controller 101 is further configured to determine an optimal amount of the skincare product formulation specific to the user, for application to the user's skin, and to control the dispenser to dispense that optimal amount.

In embodiments, the device 100 further comprises one or more spectral sensors 103a, 103b, configured to generate the spectral data 105a, 105b, by sensing light at frequency bands both inside and outside of the visible spectrum reflected from, or emitted by, the skin of the user. In some embodiments, the spectral data 105a, 105b, comprises hyperspectral data.

Alternatively or in addition, in embodiments, the controller 101 is configured to receive spectral data 105a, 105b, generated by, and transmitted from, a remote sensing device configured to sense light at frequency bands both inside and outside of the visible spectrum reflected from, or emitted by, the skin of the user.

In embodiments, the device 100 further comprises a user interface 113, wherein the user interface 113 is configured to enable the user to input one or more user requirements, and wherein the controller 101 is configured to receive the user requirements and to adjust the skincare product formulation specific to the user based on the received user requirements.

In embodiments, the user requirements comprise anticipated exposure to one or more of heat, UV radiation, pollution, humidity or other environmental factor.

In embodiments, the anticipated exposure is over a 24 hour, or 48 hour period.

In embodiments, the controller 101 is further configured to cause the user interface 113 to display information associated with the skincare product formulation specific to the user.

FIG. 19 shows a flow chart illustrating the steps of a method 1900 of dispensing a skincare product, according to embodiments of the present disclosure.

A first step of method 1900, represented by item 1901, comprises receiving at the controller 101 spectral data 105a, 105b, associated with the skin of a user.

A second step of method 1900, represented by item 1903, comprises processing the spectral data 105a, 105b, to identify one or more metabolic constituents or features of the skin of the user.

A third step of method 1900, represented by item 1905, comprises, on the basis of the identified one or more metabolic constituents or features of the skin of the user, determining a skincare product formulation specific to the user.

A fourth step of method 1900, represented by item 1907, comprises mixing and dispensing a skincare product according to the determined skincare product formulation specific to the user.

A fifth optional step of method 1900, represented by item 1909, comprises adjusting the skincare product formulation periodically, based on one or more user requirements for the skincare product formulation.

In embodiments, the step of processing the spectral data 105a, 105b, comprises using a trained classification algorithm to identify one or more metabolic constituents or features of the skin of the user.

Whilst the present disclosure has been described and illustrated with reference to particular embodiments, it will be appreciated by those of ordinary skill in the art that the present disclosure lends itself to many different variations not specifically illustrated herein. By way of example only, certain possible variations will now be described.

Whilst FIGS. 2 to 4 illustrate three examples of embodiments according to the present disclosure, it will be appreciated that other form factors and numbers of sensors and/or light sources are also possible. In particular, in each case may the skincare device may comprise greater or fewer sensors and/or light sources. In particular, although the illustrated examples each have the same number of sensors as light sources, it will be appreciated that this need not necessarily be the case. In other embodiments, the skincare device has a different number of sensors to light sources. Similarly, in embodiments, the skincare device may comprise other form factors not specifically illustrated. For example, the skincare device may comprise a desk lamp, a floor lamp, or a purpose-built scanner unit.

Embodiments of the present disclosure provide a skincare device comprising:

a light source configured to emit light onto a first portion of a user's skin and onto a second portion of the user's skin; and a controller configured to control the light source to emit light having one or more first parameters onto the first portion and light having one or more second different parameters onto the second portion.

Embodiments of the present disclosure provide a skincare device comprising:

a light source configured to emit light onto a user's skin;

a sensor configured to sense intensities of light at a plurality of wavelengths reflected from the user's skin; and a controller configured to:

on the basis of the sensed intensities, identify at least one wavelength of light for which the sensed intensity deviates from a predetermined intensity threshold, and control the light source to modify light emission at the identified at least one wavelength.

Although the embodiments described above relate to a skincare device, other embodiments of the present disclosure relate to devices other than skincare devices (for example, haircare devices, oral care devices, and floorcare devices). It will be appreciated by the skilled person that embodiments of the present disclosure may also may be used in other contexts not specifically described.

Embodiments of the present disclosure provide a device comprising:

a first sensor configured to capture a first image of a body part of a user at one or more first wavelengths;

a second sensor configured to capture a second image of the body part at one or more further wavelengths different from the one or more first wavelengths; and a controller configured to combine the first image and the second light image to generate a composite image representative of the body part.

In embodiments, the device comprises a skincare device. In such embodiments, it may be that the body part comprises the user's skin. Alternatively, the device may comprise a haircare device. In such embodiments, it may be that the body part comprises the user's hair. Alternatively, the device may comprise an oralcare device (for example, a toothbrush and/or a flossing device). In such embodiments, it may be that the body part comprises at least a part of the user's mouth.

In embodiments, the one or more wavelengths are within the visible spectrum. In embodiments, the one or more further wavelengths are outside of the visible spectrum.

Embodiments of the present disclosure provide a device comprising:

a sensor of a first type, configured to sense, in a first frequency band, one or more characteristics of subject; and a classifier trained using:

a sensor of the first type, configured to sense, in the first frequency band, one or more characteristics of the subject, and a sensor of a second type, configured to sense, in a different second frequency band, a moisture content of the subject;

a controller configured to:

provide the sensed one or more characteristics of the subject to the trained classifier;

operate the trained classifier to determine a moisture content of the subject; and control the device to perform an action associated with the determined moisture content.

In embodiments, the device comprises a skincare device. In such embodiments, it may be that the subject comprises a user's skin. Alternatively, the device may comprise a haircare device (for example, a hair straightening device and/or a hair curling device). In such embodiments, it may be that the subject comprises a user's hair. Alternatively, the device may comprise a floorcare device (for example, a vacuum cleaner or carpet cleaner). In such embodiments, it may be that the subject comprises an area of floor.

It will be appreciated that skincare device 100 may comprise one or more processors and/or memory. Thus, in embodiments, skincare device 100 comprises processor 119 and associated memory 121. Processor 119 and associated memory 221 may be configured to perform one or more of the above-described functions of skincare device 100. Each device, module, component, machine or function as described in relation to any of the examples described herein (for example, controller 101, sensors 103, light sources 109, user interface 113, or transceiver 117) may similarly comprise a processor or may be comprised in apparatus comprising a processor. One or more aspects of the embodiments described herein comprise processes performed by apparatus. In some examples, the apparatus comprises one or more processors configured to carry out these processes. In this regard, embodiments may be implemented at least in part by computer software stored in (non-transitory) memory and executable by the processor, or by hardware, or by a combination of tangibly stored software and hardware (and tangibly stored firmware). Embodiments also include computer programs, particularly computer programs on or in a carrier, adapted for putting the above-described embodiments into practice. The program may be in the form of non-transitory source code, object code, or in any other non-transitory form suitable for use in the implementation of processes according to embodiments. The carrier may be any entity or device capable of carrying the program, such as a RAM, a ROM, or an optical memory device, etc.

The one or more processors of skincare device 100 may comprise a central processing unit (CPU). The one or more processors may comprise a graphics processing unit (GPU). The one or more processors may comprise one or more of a field programmable gate array (FPGA), a programmable logic device (PLD), or a complex programmable logic device (CPLD). The one or more processors may comprise an application specific integrated circuit (ASIC). It will be appreciated by the skilled person that many other types of device, in addition to the examples provided, may be used to provide the one or more processors. The one or more processors may comprise multiple co-located processors or multiple disparately located processors. Operations performed by the one or more processors may be carried out by one or more of hardware, firmware, and software.

The one or more processors may comprise data storage. The data storage may comprise one or both of volatile and non-volatile memory. The data storage may comprise one or more of random access memory (RAM), read-only memory (ROM), a magnetic or optical disk and disk drive, or a solid-state drive (SSD). It will be appreciated by the skilled person that many other types of memory, in addition to the examples provided, may also be used. It will be appreciated by a person skilled in the art that the one or more processors may each comprise more, fewer and/or different components from those described.

The techniques described herein may be implemented in software or hardware, or may be implemented using a combination of software and hardware. They may include configuring an apparatus to carry out and/or support any or all of techniques described herein. Although at least some aspects of the examples described herein with reference to the drawings comprise computer processes performed in processing systems or processors, examples described herein also extend to computer programs, for example computer programs on or in a carrier, adapted for putting the examples into practice. The carrier may be any entity or device capable of carrying the program. The carrier may comprise a computer readable storage media. Examples of tangible computer-readable storage media include, but are not limited to, an optical medium (e.g., CD-ROM, DVD-ROM or Blu-ray), flash memory card, floppy or hard disk or any other medium capable of storing computer-readable instructions such as firmware or microcode in at least one ROM or RAM or Programmable ROM (PROM) chips.

Where in the foregoing description, integers or elements are mentioned which have known, obvious or foreseeable equivalents, then such equivalents are herein incorporated as if individually set forth. Reference should be made to the claims for determining the true scope of the present disclosure, which should be construed so as to encompass any such equivalents. It will also be appreciated by the reader that integers or features of the present disclosure that are described as preferable, advantageous, convenient or the like are optional and do not limit the scope of the independent claims. Moreover, it is to be understood that such optional integers or features, whilst of possible benefit in some embodiments of the present disclosure, may not be desirable, and may therefore be absent, in other embodiments.

The invention claimed is:

1. A skincare device comprising:
a spectral sensor configured to capture a spectral image of a subject at one or more wavelengths outside of the visible spectrum; and
a controller configured to:
analyse the spectral image to determine a measure of cosmetic residue present on the subject; and
control the skincare device to perform an action associated with the determined measure of cosmetic residue.

2. The device according to claim 1, wherein determining the measure of cosmetic residue comprises identifying a portion of the spectral image having the lowest received signal strength at the one or more wavelengths.

3. The device according to claim 2, wherein the controller is configured to determine, for each of one or more further portions of the spectral image, a relative quantity of cosmetic residue by calculating a relative signal strength compared to the identified lowest signal strength.

4. The device according to claim 1, wherein the analysis is performed in relation to a calibration image.

5. The device according to claim 4, wherein the controller is configured to capture the calibration image during a calibration procedure initiated by the user.

6. The device according to claim 4, wherein the calibration image is pre-stored in a memory on the device.

7. The device according to claim 1, wherein the subject comprises a user's skin.

8. The device according to claim 1, wherein the action comprises adjusting one or more operating settings of the skincare device.

9. The device according to claim 1, wherein the action comprises generating an alert, wherein the alert comprises one or more of: a visible alert, an audible alert, and a tactile alert.

10. The device according to claim 1, wherein:
the device comprises a light source configured to emit light onto the user's skin; and
the action comprises controlling one or more parameters of light emission by the light source.

11. The device according to claim 1, wherein the action comprises providing an output to a user interface.

12. The device according to claim 11, wherein:
the subject comprises a user's face;
the output comprises an indication of a location on the user's face of the cosmetic residue; and
the action comprises causing the user interface to display an image of a face highlighting the indicated location.

13. The device according to claim 12, wherein the image comprises an image of the user's face.

14. The device according to claim 12, wherein the image comprises a generic image of a user's face.

15. The device according to claim 11, wherein the skincare device comprises the user interface.

16. The device according to claim 11, wherein: the user interface is provided by a separate computing device; and providing the output comprises transmitting to the separate computing device a signal indicative of the output.

17. A method of operating a skincare device, the method comprising:
capturing a spectral image of a subject at one or more wavelengths outside of the visible spectrum; and
analysing the spectral image to determine a measure of cosmetic residue present on the subject; and
controlling the skincare device to perform an action associated with the determined measure of cosmetic residue.

18. A non-transitory computer-readable medium comprising a set of instructions, which, when executed by a computerised device, cause the computerised device to perform a method of operating a skincare device, the method comprising:
capturing a spectral image of a subject at one or more wavelengths outside of the visible spectrum; and
analysing the spectral image to determine a measure of cosmetic residue present on the subject; and
controlling the skincare device to perform an action associated with the determined measure of cosmetic residue.

* * * * *